(12) United States Patent
Kishida et al.

(10) Patent No.: US 9,283,354 B2
(45) Date of Patent: Mar. 15, 2016

(54) CATHETER

(75) Inventors: Manabu Kishida, Settsu (JP); Yoichi Haga, Sendai (JP)

(73) Assignee: KANEKA CORPORATION, Osaka (JP)

( * ) Notice: Subject to any disclaimer, the term of this patent is extended or adjusted under 35 U.S.C. 154(b) by 927 days.

(21) Appl. No.: 12/739,821

(22) PCT Filed: Oct. 24, 2008

(86) PCT No.: PCT/JP2008/069327
§ 371 (c)(1),
(2), (4) Date: Apr. 26, 2010

(87) PCT Pub. No.: WO2009/054491
PCT Pub. Date: Apr. 30, 2009

(65) Prior Publication Data
US 2010/0249824 A1 Sep. 30, 2010

(30) Foreign Application Priority Data

Oct. 27, 2007 (JP) ................. 2007-279719

(51) Int. Cl.
*A61M 25/10* (2013.01)
*A61M 25/01* (2006.01)

(52) U.S. Cl.
CPC ....... *A61M 25/0122* (2013.01); *A61M 25/0155* (2013.01); *A61M 25/1002* (2013.01); *A61M 2025/1084* (2013.01)

(58) Field of Classification Search
CPC ............... A61M 25/0122; A61M 25/0133; A61M 25/0155; A61M 2025/1084
USPC ............... 606/108, 191, 192, 194; 604/103.05
See application file for complete search history.

(56) References Cited

U.S. PATENT DOCUMENTS 3,773,034 A * 11/1973 Burns et al. .................. 600/434
4,906,230 A * 3/1990 Maloney et al. ........... 604/95.03
4,976,191 A 12/1990 Suzumori et al.
(Continued)

FOREIGN PATENT DOCUMENTS

JP 63-35225 2/1988
JP 2-58451 4/1990
(Continued)

OTHER PUBLICATIONS

English translation of the International preliminary report on patentability (Chapter 1) of PCT Application No. PCT/JP2008/069327.
(Continued)

*Primary Examiner* — Katherine Rodjom
(74) *Attorney, Agent, or Firm* — Nixon & Vanderhye, PC

(57) ABSTRACT

In order to provide a catheter which can be operated even when it is deformed inside a bent blood vessel and whose movable part can be easily bent and the movable part thus bent is firmly kept in this shape, a catheter includes: a fluid-driven actuator including: a balloon; a restricting member for restricting inflation of the balloon in a short axis direction of the catheter; and a tube which is less stretchable in a long axis direction of the catheter than the balloon is, according to a cross-sectional view of the fluid-driven actuator taken along the short axis direction of the catheter, the tube being eccentrically provided with respect to the restricting member.

6 Claims, 15 Drawing Sheets

(56) References Cited

U.S. PATENT DOCUMENTS

| | | | | |
|---|---|---|---|---|
| 5,556,382 | A | * | 9/1996 | Adams .................. 604/103.09 |
| 5,577,992 | A | * | 11/1996 | Chiba et al. ................. 600/152 |
| 5,860,914 | A | | 1/1999 | Chiba et al. |
| 6,261,260 | B1 | | 7/2001 | Maki et al. |
| 6,478,772 | B2 | | 11/2002 | Maki et al. |
| 6,579,260 | B2 | | 6/2003 | Maki et al. |
| 2001/0016727 | A1 | | 8/2001 | Maki et al. |
| 2001/0044597 | A1 | | 11/2001 | Maki et al. |
| 2006/0074372 | A1 | | 4/2006 | Haga et al. |
| 2007/0106245 | A1 | * | 5/2007 | McQueen et al. ........... 604/508 |
| 2007/0270781 | A1 | * | 11/2007 | Burgermeister et al. ..... 604/528 |

FOREIGN PATENT DOCUMENTS

| | | |
|---|---|---|
| JP | 4-8337 | 1/1992 |
| WO | 2004/050160 | 6/2004 |
| WO | 2007/082189 | 7/2007 |

OTHER PUBLICATIONS

International Search Report for PCT/JP2008/069327, mailed Dec. 2, 2008.

M. Kishida et al. "Active Bending Catheter . . . " Conference of Japanese Society for Medical and Biological Engineering (CD-ROM), Japan, 2011.

* cited by examiner

CATHETER

This application is the U.S. national phase of International Application No. PCT/JP2008/069327 filed 24 Oct. 2008, which designated the U.S. and claims priority to Japan Application No. 2007-279719 filed 27 Oct. 2007, the entire contents of each of which are hereby incorporated by reference.

TECHNICAL FIELD

The present invention relates to a medical catheter. In particular, the present invention relates to a catheter used in percutaneous transluminal angioplasty (PTA) and percutaneous transluminal coronary angioplasty (PTCA), which are performed for peripheral blood vessel shaping, coronary artery shaping, valve shaping, and the like.

BACKGROUND ART

Conventionally, percutaneous transluminal angioplasty (PTA) and percutaneous transluminal coronary angioplasty (PTCA) have been widely used for treatment (expansion) of a narrowed site, obstruction site, or the like site of an intravascular lumen so as to restore or improve a bloodstream in a coronary artery, a peripheral vessel, or the like.

An example of general PTCA employing a balloon catheter is described below. First, a guiding catheter is inserted from a puncture site in a femoral artery, a brachial artery, or a radial artery. The guiding catheter is then inserted more deeply into an aorta, until a distal end of the guiding catheter is positioned at an entrance to a coronary artery. Next, a guide wire, which extends through a guidewire lumen, is inserted into the coronary artery until a distal end of the guide wire is positioned beyond the narrowed site of the coronary artery. Then, the balloon catheter is inserted along the guide wire so that a balloon of the balloon catheter is positioned at the narrowed site. Thereafter, the balloon is inflated by pressure fluid which is supplied, via an inflation lumen, from a device such as an indeflator. The balloon thus inflated expands the narrowed site. After the narrowed site is expanded, the balloon is deflated by reducing pressure inside the balloon, and then removed from the living body. In this way, PTCA is completed.

For a lesion such as that having a severely narrowed site or a chronic total obstruction, it may be impossible to insert the guide wire so that its distal end is positioned beyond the narrowed site. Accordingly, it may be impossible to treat such a lesion. If this is the case, a microcatheter or a penetration catheter is used. These catheters make it possible to insert the guide wire until the distal end thereof is positioned beyond the narrowed site.

Further, in performing PTCA, it may be necessary to locally administer a therapeutic agent to the narrowed site. An example of such a treatment is a treatment whereby to locally administer a thrombolytic agent to the narrowed site so as to lyse a thrombus. In performing this treatment, an infusion catheter is used. The infusion catheter is capable of locally administering the therapeutic agent to the narrowed site.

Among lesions to be treated by using a medical expansion catheter, specific lesions are a chronic total obstruction (CTO) lesion in the coronary artery, a lesion at a sharp bifurcation, a lesion at an entrance to a bifurcation, and the like. For such lesions, it is extremely difficult to insert the guide wire so that the distal end thereof is positioned beyond an affected site prior to the expansion treatment.

In order to treat the above specific lesions by inserting the guide wire, it is required to design the catheter in a devised manner so that the distal end thereof can be actively bent.

Patent Literature 1 discloses a catheter having an bending part at a distal end of an insertion section, wherein the bending part is driven by an operation wire extending from a distal end to a proximal end of the catheter. However, when the catheter is inserted into a peripheral vessel having a sharp curve, the catheter is deformed and thus the operation wire is subjected to large friction resistance. Accordingly, it may be impossible to manually operate the bending part in a desired manner.

In order to solve this problem, there have been considered a variety of methods for actively driving the distal end of the catheter without using the operation wire.

Patent Literature 2 discloses a medical tube having a movable part, which is bent by using pressure fluid. The movable part is bent by making use of a difference between a length of part of the balloon and a length of another part of the balloon, which difference occurs when the pressure fluid is injected into the medical tube. That is, the movable part of the medical tube is bent by (i) generating partial force in a long axis direction of the medical tube and (ii) making use of the force thus generated. However, since the balloon expands both in the long axis direction and a short axis direction, it is not possible to efficiently generate the force in the long axis direction of the medical tube. In addition, an external diameter of the movable part increases as an angle at which the movable part is bent becomes sharp.

Patent Literature 3 discloses an actuator constituted by (i) a noncircular tube that is elastically deformable and (ii) a member that is not so elastically deformable as the noncircular tube. The noncircular tube and the member are provided along with each other in an axial direction so as to form an integral structure of the actuator. The actuator is bent so that the member is positioned inside the noncircular tube, by adjusting pressure in the noncircular tube. However, the feature of the actuator disclosed in Patent Literature 3 lies in a shape of the noncircular tube, and thus the noncircular tube is limited as to its shape. Therefore, in a case where the actuator is put into medical use for example as a constituent part of the catheter, the actuator may damage a blood vessel or may be inconvenient for use because of its specified external diameter etc.

Patent Literature 4 discloses a cylindrical catheter that can be moved by using the pressure fluid. The catheter has a movable part, inside of which an aperture of a tube is positioned. The aperture of the tube can be operated by making use of force in the long axis direction of the catheter. More specifically, the catheter disclosed in Patent Literature 4 includes an elastic tube and an expansion controlling body for controlling expansion of the elastic tube. The elastic tube is provided uniformly inside the expansion controlling body. That is, the expansion controlling body is provided so as to cover an outer surface of the elastic tube. However, it is not possible to surely specify a direction in which the catheter is bent with use of the above two bodies alone. Therefore, the catheter of Patent Literature 4 further includes a cord-like body, which specifies the direction in which the catheter is bent.

However, in the catheter of Patent Literature 4, a position of the tube provided inside the movable part is unstable with respect to a position of the catheter. Accordingly, the tube may hinder the movable part from being bent, thereby hindering efficient movement of the catheter. Further, the expansion controlling body, which controls the tube from expanding in the short axis direction due to injection of the pressure fluid, is not optimized so that the tube is easily expanded and contracted in the long axis direction. Accordingly, the expansion controlling body is not capable of efficiently transducing expansion force of the balloon into force in the long axis direction. Therefore, the movable part cannot firmly keep a bent shape.

CITATION LIST

Patent Literature 1
Japanese Unexamined Utility Model Registration Application Publication, Jitsukaihei, No. 2-58451
Patent Literature 2
Japanese Patent Application Publication, Tokukaihei, No. 11-405 A
Patent Literature 3
Japanese Patent No. 2993506
Patent Literature 4
U.S. Pat. No. 3,773,034

SUMMARY OF INVENTION

The present invention has been made in view of the problems, and an object thereof is providing a catheter (i) which can be operated even when it is deformed inside a bent blood vessel, (ii) whose movable part can be easily bent, and (iii) the movable part thus bent is firmly kept in this shape.

(1) A catheter of the present invention includes: a fluid-driven actuator including: a balloon; a restricting member for restricting inflation of the balloon in a short axis direction of the catheter; and a tube which is less stretchable in a long axis direction of the catheter than the balloon is, according to a cross-sectional view of the fluid-driven actuator taken along the short axis direction of the catheter, the tube being eccentrically provided with respect to the restricting member.

According to the configuration, it is possible to drive and operate the catheter even in a case where the catheter is deformed inside a peripheral blood vessel having a sharp curve. This is because a flow path for pressure fluid is secured even in the case where the catheter is deformed. Further, since the tube is eccentrically provided with respect to the restricting member (for example, the tube is eccentrically provided on one side of the restricting member), the tube can be easily bent by small expansion of the balloon in the long axis direction of the catheter. Furthermore, according to the cross-sectional view taken along the short axis direction of the catheter, a neutral surface is positioned near the one side of the restricting member. This makes it possible to reduce a percentage of areas of regions not contributing to bending, with respect to a total area of the balloon (for example, see FIG. 15). The neutral surface in the Specification is defined as follows. According to the cross-sectional view taken along the short axis direction of the catheter, there is a line existing in the middle of the catheter which line undergoes no strain even when the catheter is bent. A horizontal plane including the line is referred to as the neutral surface in the Specification (refer to page 69 of New Mechanical Engineering Series Material Mechanics, Asakura Publishing Co., Ltd, (*Shin kikai kougaku sirizu zairyou rikigaku, asakura shoten*) 15$^{th}$ Impression). Specifically, when the catheter is bent, the movable part undergoes strain in a tensile direction on its outside, while it undergoes strain in a compression direction on its inside. According to the cross-sectional view taken along the short axis direction of the catheter, there is a line which undergoes neither the strain in the tensile direction nor the strain in the compression direction. The horizontal plane including the line is defined as the neutral surface. As described above, according to the cross-sectional view taken along the short axis direction of the catheter, the neutral surface is positioned near the one side of the restricting member. This makes it possible to increase a percentage of an area of a region contributing to bending, which exists on a side opposite to the one side of the restricting member, with respect to the total area of the balloon. Accordingly, the movable part can be efficiently and easily bent by low fluid pressure. Further, the movable part thus bent is firmly kept in this shape by increasing the fluid pressure. It should be noted in the Specification that the "long axis direction of the catheter" means a direction in which the catheter extends, whereas the "short axis direction of the catheter" means a direction perpendicular to the long axis direction of the catheter. Further, the "cross-sectional surface taken along a short axis direction of the catheter" in the Specification means a cross-sectional surface taken along a plane perpendicular to the long axis of the catheter. Furthermore, the restricting member restricts the inflation of the tube in the short axis direction of the catheter. Accordingly, it is possible to efficiently transduce expansion force of the balloon into force in the long axis direction of the catheter. Moreover, according to the configuration, a direction in which the movable part is bent can be specified by using only a small number of members.

(2) The catheter of the present invention is preferably configured such that the restricting member is a coil.

According to the configuration, the restricting member can be easily produced.

(3) The catheter of the present invention is preferably configured such that at least part of the balloon and at least part of the tube are provided inside the coil.

According to the configuration, the balloon is provided inside the coil (in other words, inside a cylinder hollow of the coil). Accordingly, when the balloon inflates, it is possible to easily hinder the inflation of the balloon in the short axis direction of the catheter. The balloon, which is hindered from inflating in the short axis direction of the catheter, then tries to inflate in the long axis direction of the catheter. As such, it is possible to more efficiently expand and contract the balloon in the long axis direction of the catheter.

(4) The catheter of the present invention is preferably configured so as to further include: an intermediate member which is less stretchable in the long axis direction of the catheter than the balloon is, according to the cross-sectional view of the fluid-driven actuator taken along the short axis direction of the catheter, the intermediate member being eccentrically provided with, respect to the fluid-driven actuator in the same direction as the tube is eccentrically provided.

According to the configuration, the neutral surface is positioned closer to the one side of the restricting member. This makes it possible to reduce the percentage of the areas of the regions not contributing to bending, with respect to the total area of the balloon (for example, see FIG. 15). As described above, according to the cross-sectional view taken along the short axis direction of the catheter, the neutral surface is positioned near the one side of the restricting member. This makes it possible to increase the percentage of the area, existing in a opposite side of the one side of the restricting member, of the region contributing to bending, with respect to the total area of the balloon. As such, the movable part can be efficiently and easily bent by low fluid pressure. Further, the movable part thus bent is firmly kept in this shape by increasing the fluid pressure.

(5) The catheter of the present invention is preferably configured such that, according to the cross-sectional view of the fluid-driven actuator taken along the short axis direction of the catheter, the intermediate member is in contact with the restricting member. A position at which the intermediate member makes contact with the restricting member is not particularly limited. For example in a case where the restricting member is in a form of a cylinder hollow, the intermediate member can be provided for example in a position which makes contact with an inner surface of the cylinder hollow.

According to the configuration, the neutral surface is positioned closer to the one side of the restricting member. This makes it possible to reduce the percentage of the areas of the regions not contributing to bending, with respect to the total area of the balloon (for example, see FIG. 15). As described above, according to the cross-sectional view taken along the short axis direction of the catheter, the neutral surface is positioned near the one side of the restricting member. This makes it possible to increase the percentage of the area, existing in the opposite side of the one side of the restricting member, of the region contributing to bending, with respect to the total area of the balloon. As such, the movable part can be efficiently and easily bent by low fluid pressure. Further, the movable part thus bent is firmly kept in this shape by increasing the fluid pressure. Moreover, it becomes possible to easily produce the catheter.

(6) The catheter of the present invention is preferably configured such that, according to the cross-sectional view of the fluid-driven actuator taken along the short axis direction of the catheter, the intermediate member is provided between the restricting member and the tube.

According to the configuration, the neutral surface is positioned closer to the one side of the restricting member. This makes it possible to reduce the percentage of the areas of the regions not contributing to bending, with respect to the total area of the balloon (for example, see FIG. 15). As described above, according to the cross-sectional view taken along the short axis direction of the catheter, the neutral surface is positioned near the one side of the restricting member. This makes it possible to increase the percentage of the area, existing in the opposite side of the one side of the restricting member, of the region contributing to bending, with respect to the total area of the balloon. As such, the movable part can be efficiently and easily bent by low fluid pressure. Further, the movable part thus bent is firmly kept in this shape by increasing the fluid pressure. Moreover, it becomes possible to easily produce the catheter.

(7) The catheter of the present invention is preferably configured such that, according to the cross-sectional view of the fluid-driven actuator taken along the short axis direction of the catheter, the intermediate member is in contact with the tube.

According to the configuration, the neutral surface is positioned closer to the one side of the restricting member. This makes it possible to reduce the percentage of the areas of the regions not contributing to bending, with respect to the total area of the balloon (for example, see FIG. 15). As described above, according to the cross-sectional view taken along the short axis direction of the catheter, the neutral surface is positioned near the one side of the restricting member. This makes it possible to increase the percentage of the area, existing in the opposite side of the one side of the restricting member, of the region contributing to bending, with respect to the total area of the balloon. As such, the movable part can be efficiently and easily bent by low fluid pressure. Further, the movable part thus bent is firmly kept in this shape by increasing the fluid pressure. Moreover, it becomes possible to easily produce the catheter.

(8) The catheter of the present invention is preferably configured such that the number of the intermediate member provided is plural, and according to the cross-sectional view of the fluid-driven actuator taken along the short axis direction of the catheter, at least one of the intermediate members is provided in the following position (a), (b), or (c):

(a) a position where the at least one of the intermediate members makes contact with the restricting member;

(b) a position between the restricting member and the tube; or (c) a position where the at least one of the intermediate members makes contact with the tube.

According to the configuration, the one side of the restricting member becomes less extensive in the long axis direction of the catheter when the balloon extends in the long axis direction of the catheter.

(9) The catheter of the present invention is preferably configured such that the tube includes a reinforcing layer.

According to the configuration, it is possible to improve kink resistance when the movable part is bent.

For a fuller understanding of the nature and advantages of the invention, reference should be made to the ensuing detailed description taken in conjunction with the embodiments and the accompanying drawings.

REFERENCE SIGNS LIST

1 Restricting Member
2 Balloon
3 Tube
4 Outer Shaft
5A Intermediate Member
5B Intermediate Member
5C Intermediate Member
5D(a) Intermediate Member
5D(b) Intermediate Member
5E(a) Intermediate Member
5E(b) Intermediate Member
5F(a) Intermediate Member
5F(b) Intermediate Member
5F(c) Intermediate Member
5G(a) Intermediate Member
5G(b) Intermediate Member
5H(a) Intermediate Member
5H(b) Intermediate Member
5I(a) Intermediate Member
5I(b) Intermediate Member
5J Intermediate Member
5K Intermediate Member
5L Intermediate Member
6 Reinforcing Layer
7 Neutral Surface
8 Region Contributing to Bending
9A Region Not Contributing to Bending
9B Region Not Contributing to Bending
21 Catheter
22 Movable Part (Fluid-driven Actuator)
23 Hub
24 Proximal End Aperture
25 Pressure Fluid Entrance
26 Distal End Aperture
27 Pressure Fluid Lumen

DESCRIPTION OF EMBODIMENTS

An embodiment of the present invention is described below with reference to the attached drawings. The following description deals with a microcatheter as an example. However, the present invention is not limited to the microcatheter. Examples of the catheter of the present invention encompass all kinds of catheters that are commonly known by those skilled in the art, such as: a catheter which includes a balloon, stent, or the like, and is used for treatment of a blood vessel; a catheter (including a penetration catheter) with which a guide wire is inserted for insertion of a medical device; and a guiding catheter.

[1. Configuration of Catheter]

Figure 1:
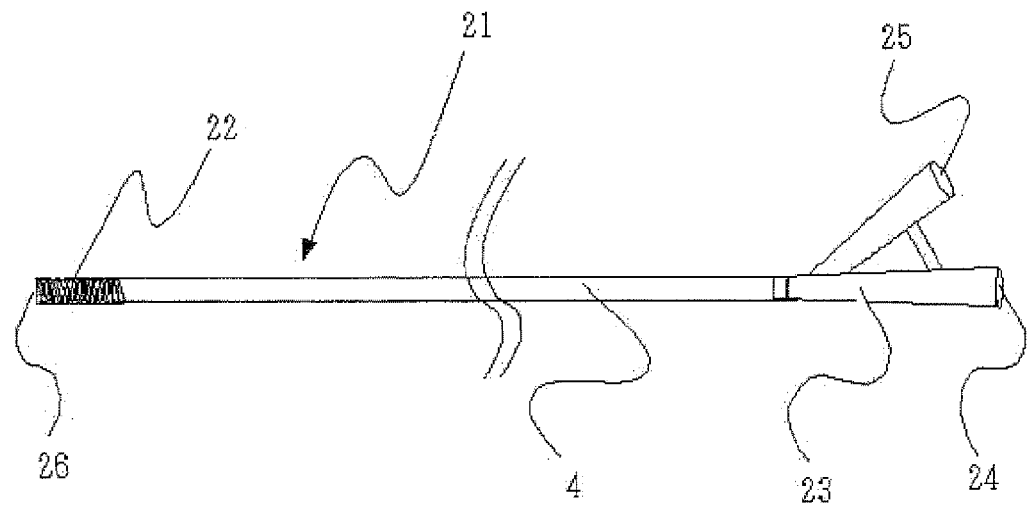
FIG. 1 schematically illustrates an overall configuration of an over-the-wire type (OTW type) catheter according to an embodiment of the present invention.
Figure 2:
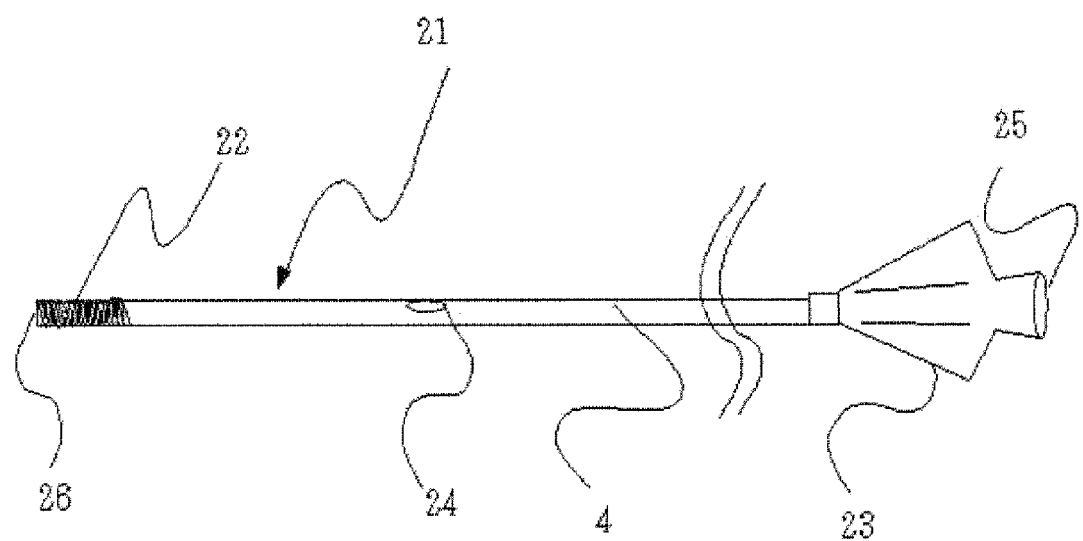
FIG. 2 schematically illustrates an overall configuration of a rapid exchange type (RX type) catheter according to the embodiment of the present invention.
Figure 3:
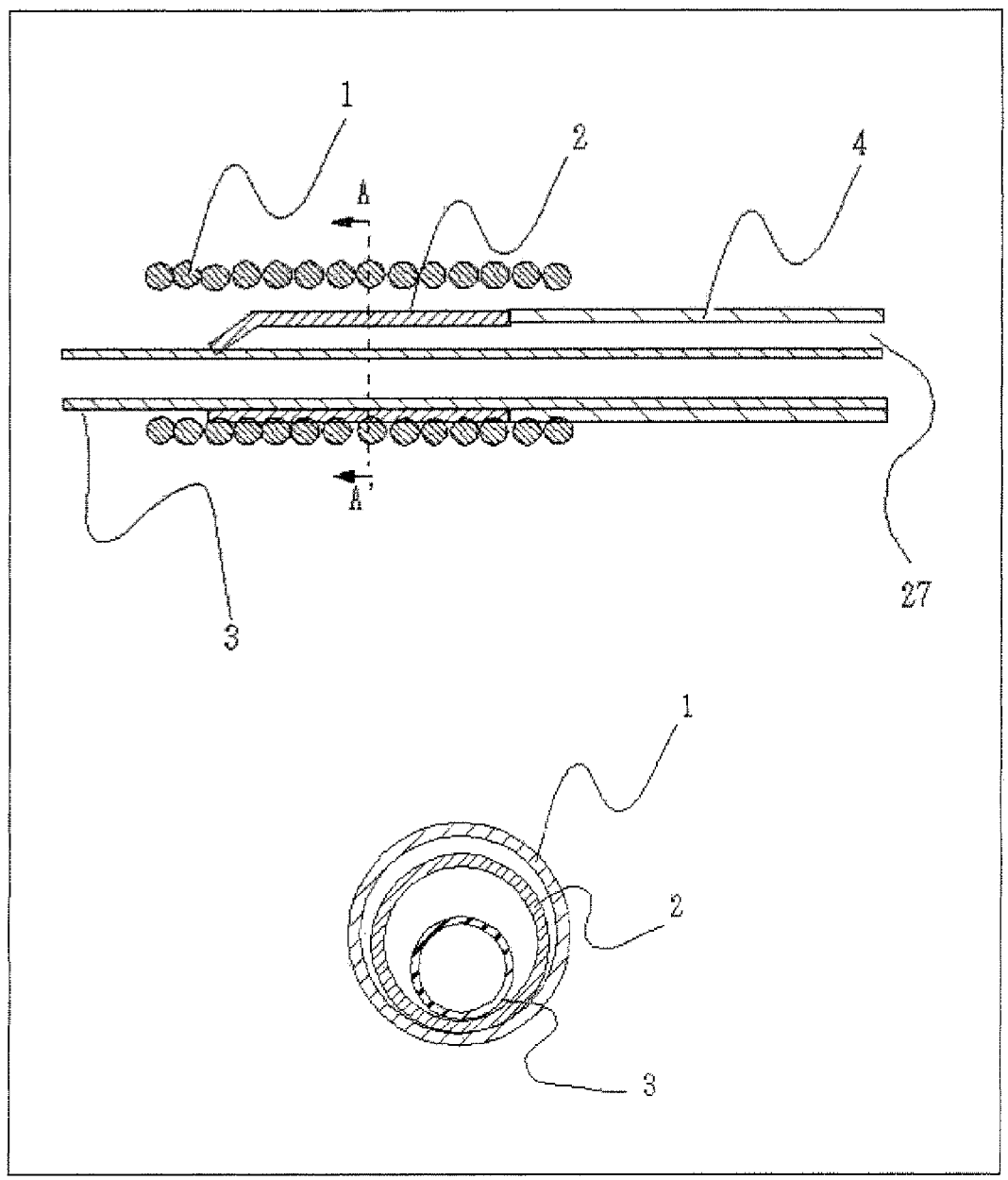
FIG. 3 illustrates (i) a cross-sectional view of a movable part of a catheter according to a first embodiment of the present invention, taken along a long axis direction of the catheter and (ii) a cross-sectional view taken along the plane A-A' in a short axis direction of the catheter.

FIG. 1 illustrates an overall configuration of an over-the-wire type (OTW type) catheter out of catheters according to embodiments of the present invention. FIG. 2 illustrates an overall configuration of a rapid exchange type (RX type) catheter out of catheters according to the embodiments of the present invention. FIG. 3 schematically illustrates (i) a cross-sectional view of a movable part of the catheter according to the embodiment of the present invention, taken along a long axis direction of the catheter, and (ii) a cross-sectional view taken along the plane A-A' in a short axis direction of the catheter.

A catheter 21 includes a movable part 22 (fluid-driven actuator), an outer shaft 4, and a hub 23.

The catheter 21 including the movable part 22 is preferably configured such that the movable part 22 is positioned at a distal end of the catheter 21. The movable part 22 includes a restricting member 1, a balloon 2, and a tube 3. The tube 3 is eccentrically provided inside and on one side of the restricting member 1. The balloon 2 is provided, inside the restricting member 1 and outside the tube 3. The balloon 2 may be provided for example so as to enclose the tube 3, as illustrated in the cross-sectional view taken along the plane A-A' of FIG. 3. Alternatively, the balloon 2 may be provided outside the tube 3 in parallel with the long axis direction of the catheter, as illustrated in the cross-sectional view taken along the plane L-L' of FIG. 14. Further, the balloon 2 preferably has a length shorter than that of the restricting member 1. The over-the-wire (OTW) type catheter as illustrated in FIG. 1 is generally configured such that the tube 3 extends continuously from a distal end aperture 26 to a proximal end aperture 24 that is provided at a proximal end of the catheter. On the other hand, the rapid exchange (RX) type catheter as illustrated in FIG. 2 is generally configured such that the tube 3 extends continuously from the distal end aperture 26 to the proximal end aperture 24 that is provided in the middle of the outer shaft 4.

The distal end aperture 26 may be positioned closer to a distal end of the catheter than a distal end of the restricting member 1 is. Alternatively, the distal end aperture 26 may be provided so that the distal end aperture 26 and the distal end of the restricting member 1 are aligned. The outer shaft 4 can be provided so that the outer shaft 4 encloses the tube 3 and extends continuously from the movable part 22 to a pressure fluid entrance 25. A pressure fluid lumen 27 can be provided between an outer surface of the tube 3 and an inner surface of the outer shaft 4. It is possible to additionally provide a pressure fluid tube as needed.

Figure 15:
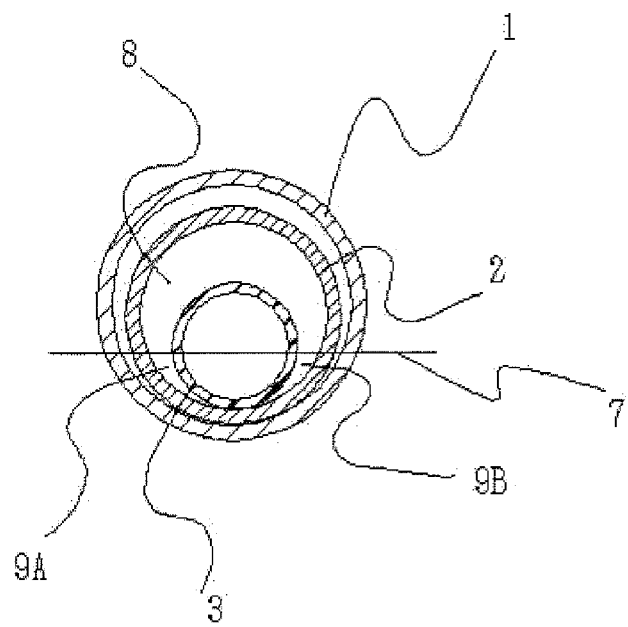
FIG. 15 is a cross-sectional view for indicating a position of a neutral surface in the movable part of the catheter according to the embodiment of the present invention.

According to the above configuration, it is possible to drive and operate the catheter 21 even in a case where the catheter 21 is deformed inside a peripheral blood vessel having a sharp curve. This is because a flow pass for the pressure fluid is secured even in the case where the catheter 21 is deformed. Further, since the tube 3 is eccentrically provided inside and on one side of the restricting member 1, the tube 3 is easily bent by small expansion, in the long axis direction of the catheter, of the balloon 2. Accordingly, the movable part 22 can be easily bent. Furthermore, according to the cross-sectional view taken along the short axis direction of the catheter, a neutral surface 7 is positioned near the one side of the restricting member 1. This makes it possible to reduce a percentage of areas of regions 9A and 9B not contributing to bending, with respect to a total area of the balloon 2. At the same time, this makes it possible to increase a percentage of a region 8 contributing to bending, which exists on a side opposite to the one side of the restricting member 1, with respect to the total area of the balloon 2 (for example, see FIG. 15). Accordingly, the movable part 22 can be easily bent. Furthermore, the movable part 22 thus bent can be firmly kept in this shape.

In addition, it is preferable to provide a radiopaque marker to the distal end aperture 26 of the catheter 21, as needed. Further, in a case where the outer surface of the restricting member 1 is uneven, the outer surface of the restricting member 1 is preferably coated with thin resin or the like. Furthermore, the restricting member 1 may have sealing agents at both ends thereof. Moreover, the movable part 22 may have a valvular function at a distal end thereof.

Figure 4:
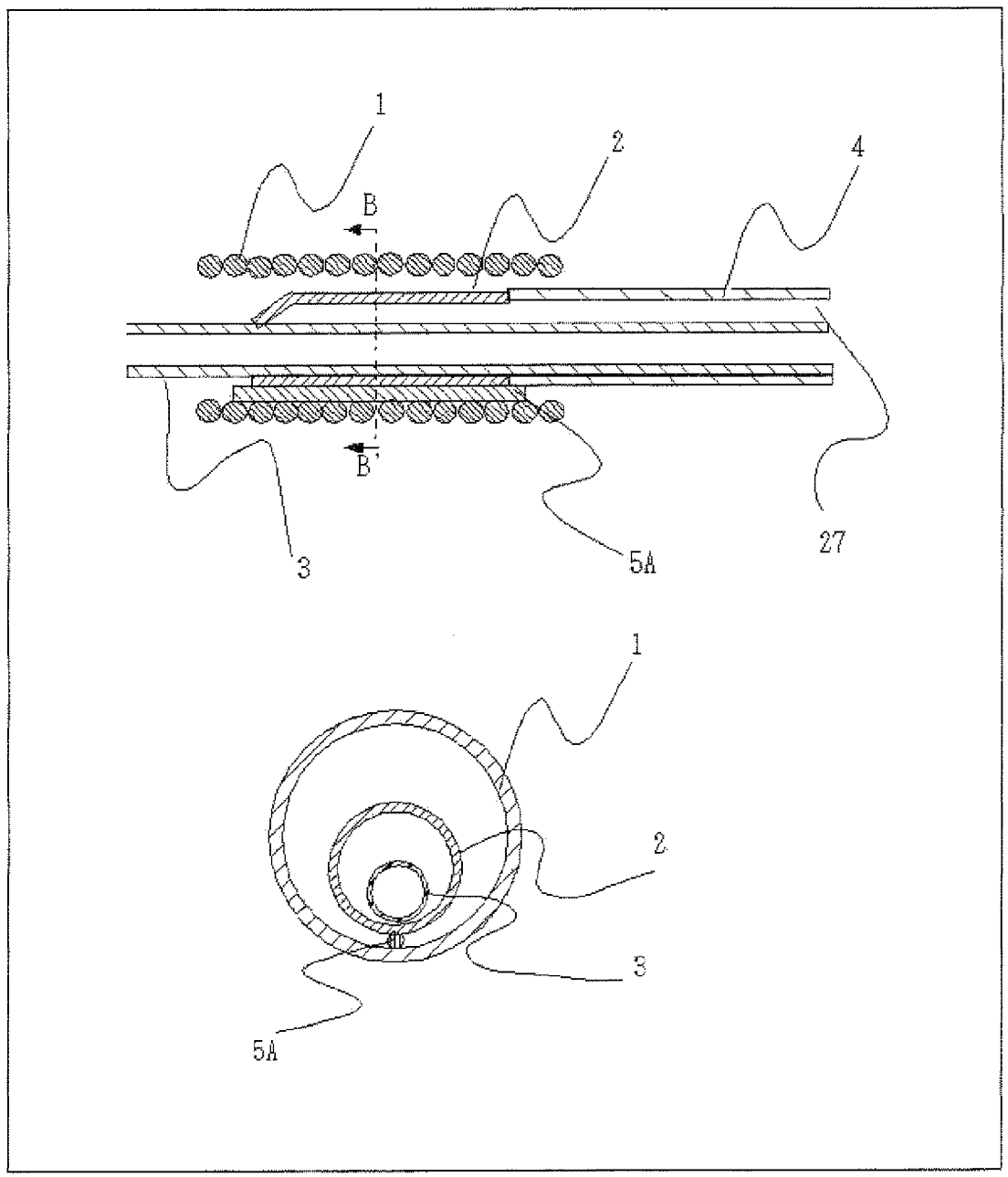
FIG. 4 illustrates (i) a cross-sectional view of a movable part of a catheter according to a second embodiment of the present invention, taken along the long axis direction of the catheter and (ii) a cross-sectional view taken along the plane B-B' in the short axis direction of the catheter.
Figure 7:
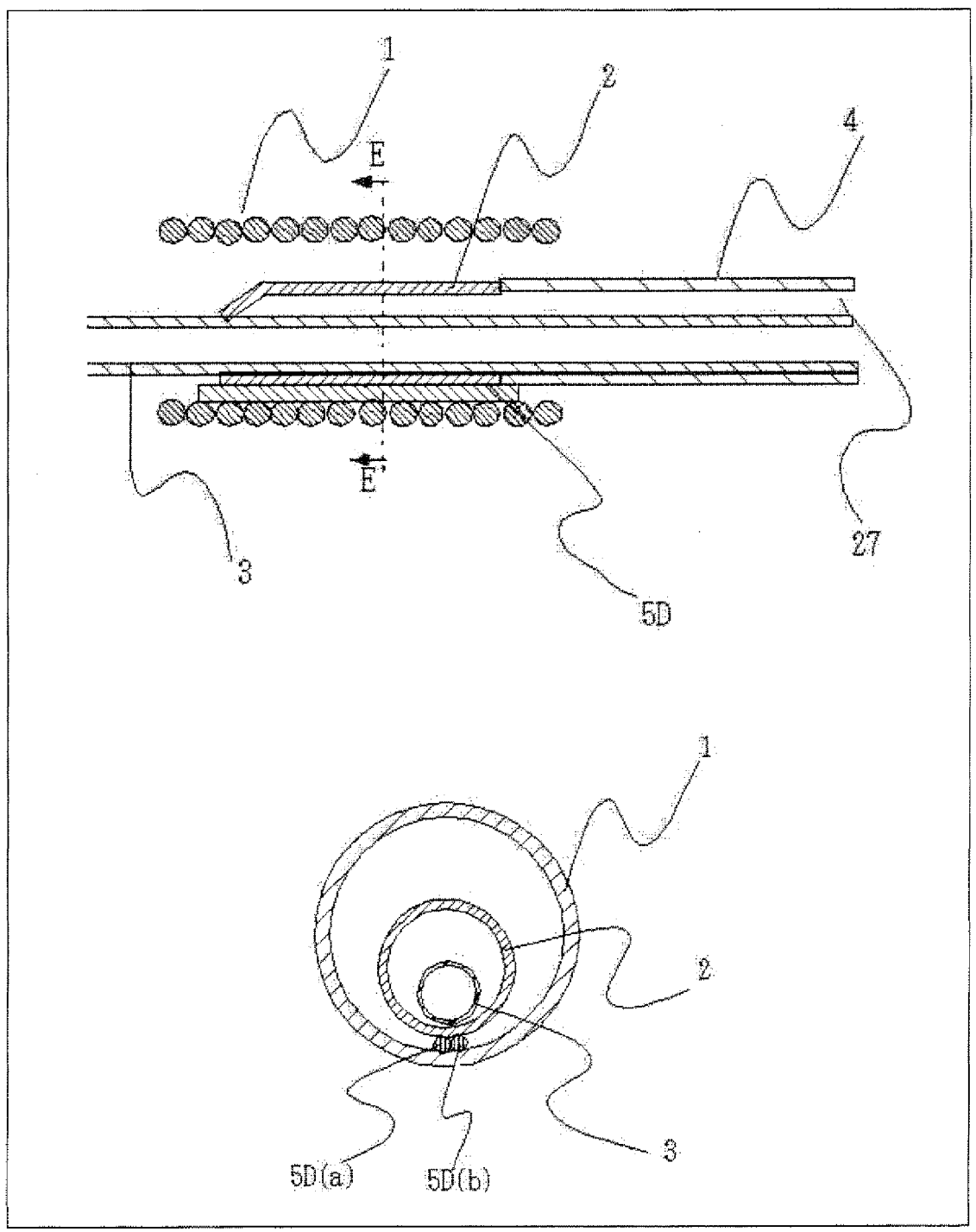
FIG. 7 illustrates (i) a cross-sectional view of a movable part of a catheter according to a fifth embodiment of the present invention, taken along the long axis direction of the catheter and (ii) a cross-sectional view taken along the plane E-E' in the short axis direction of the catheter.
Figure 8:
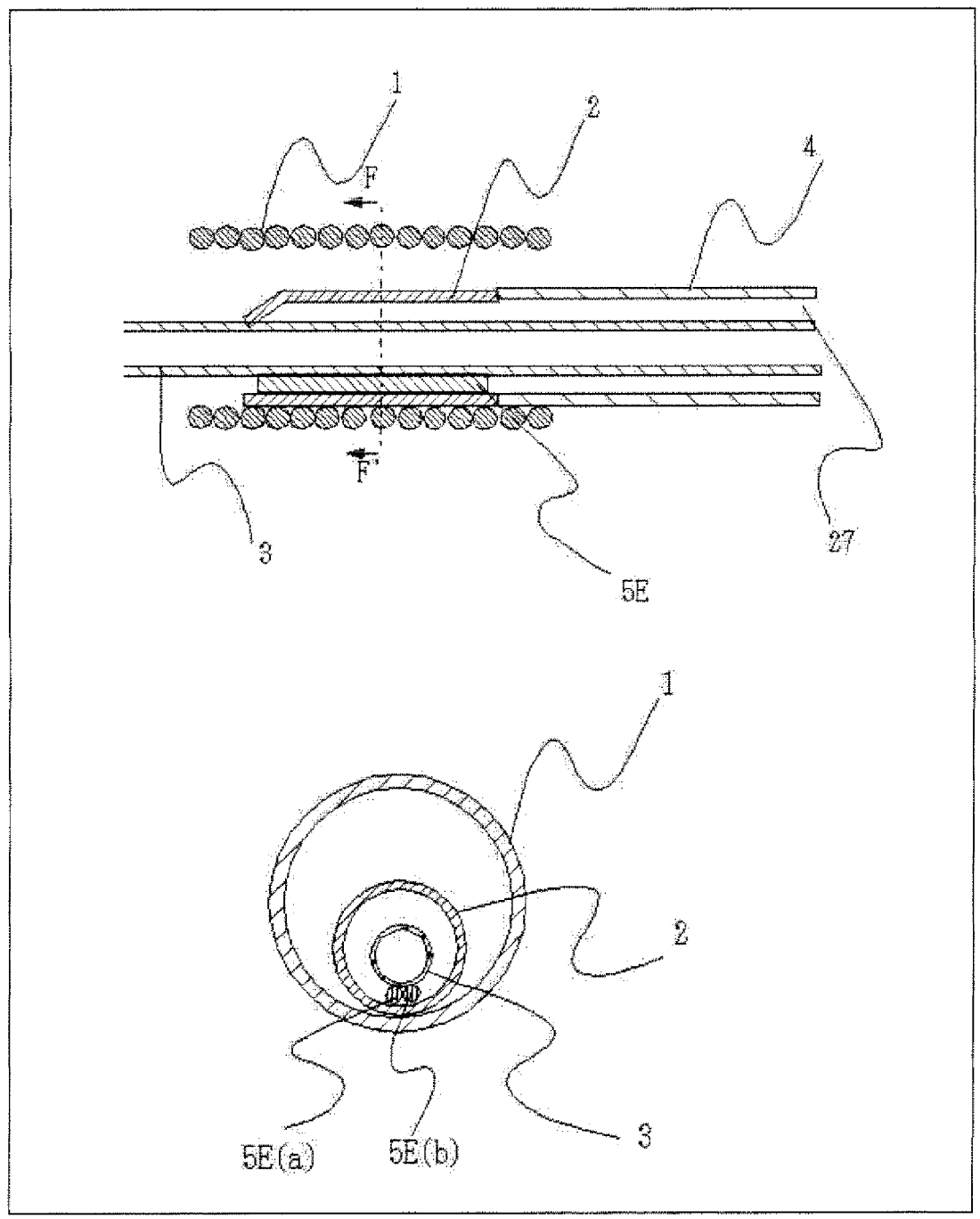
FIG. 8 illustrates (i) a cross-sectional view of a movable part of a catheter according to a sixth embodiment of the present invention, taken along the long axis direction of the catheter and (ii) a cross-sectional view taken along the plane F-F' in the short axis direction of the catheter.
Figure 9:
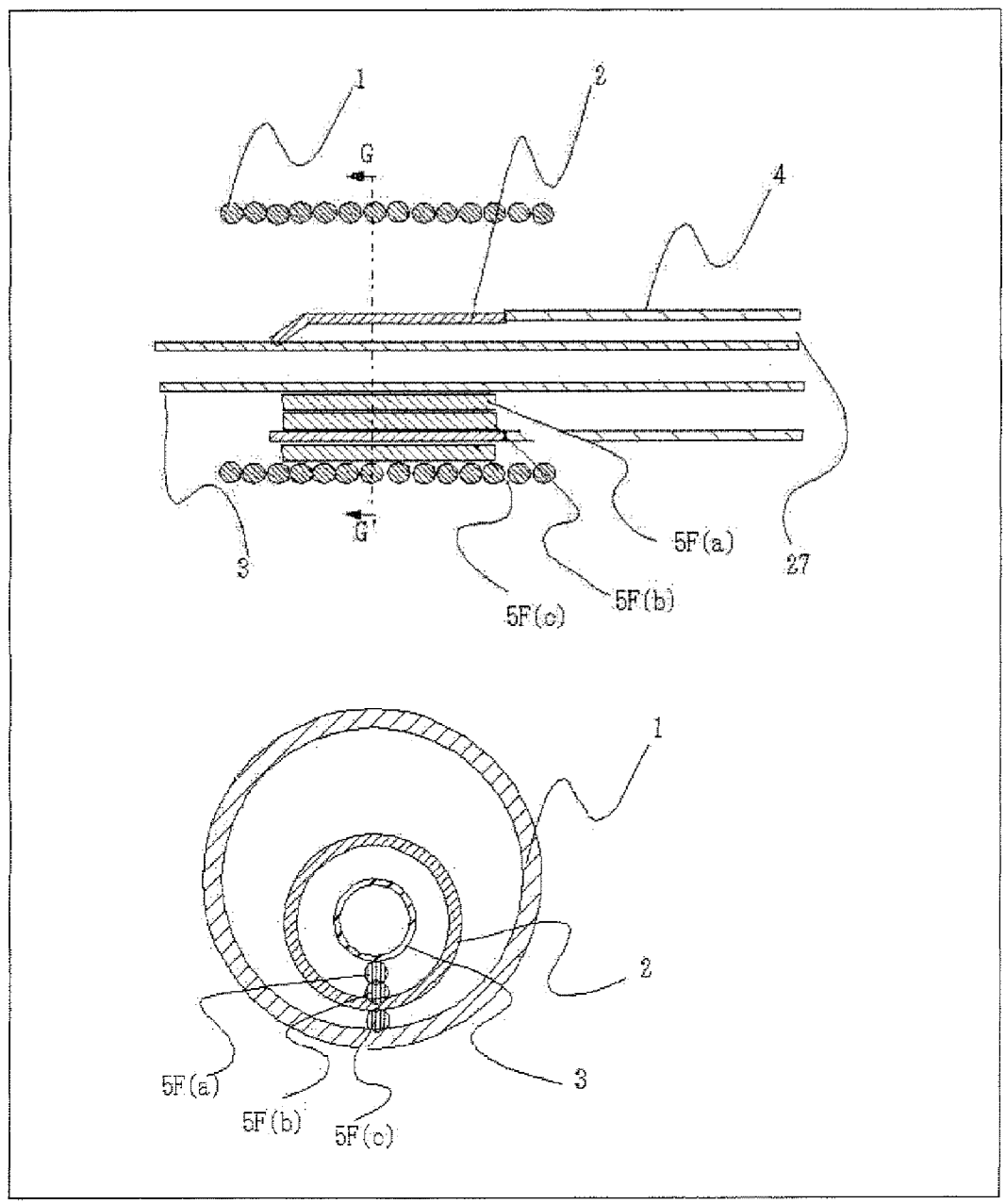
FIG. 9 illustrates (i) a cross-sectional view of a movable part of a catheter according to a seventh embodiment of the present invention, taken along the long axis direction of the catheter and (ii) a cross-sectional view taken along the plane G-G' in the short axis direction of the catheter.
Figure 10:
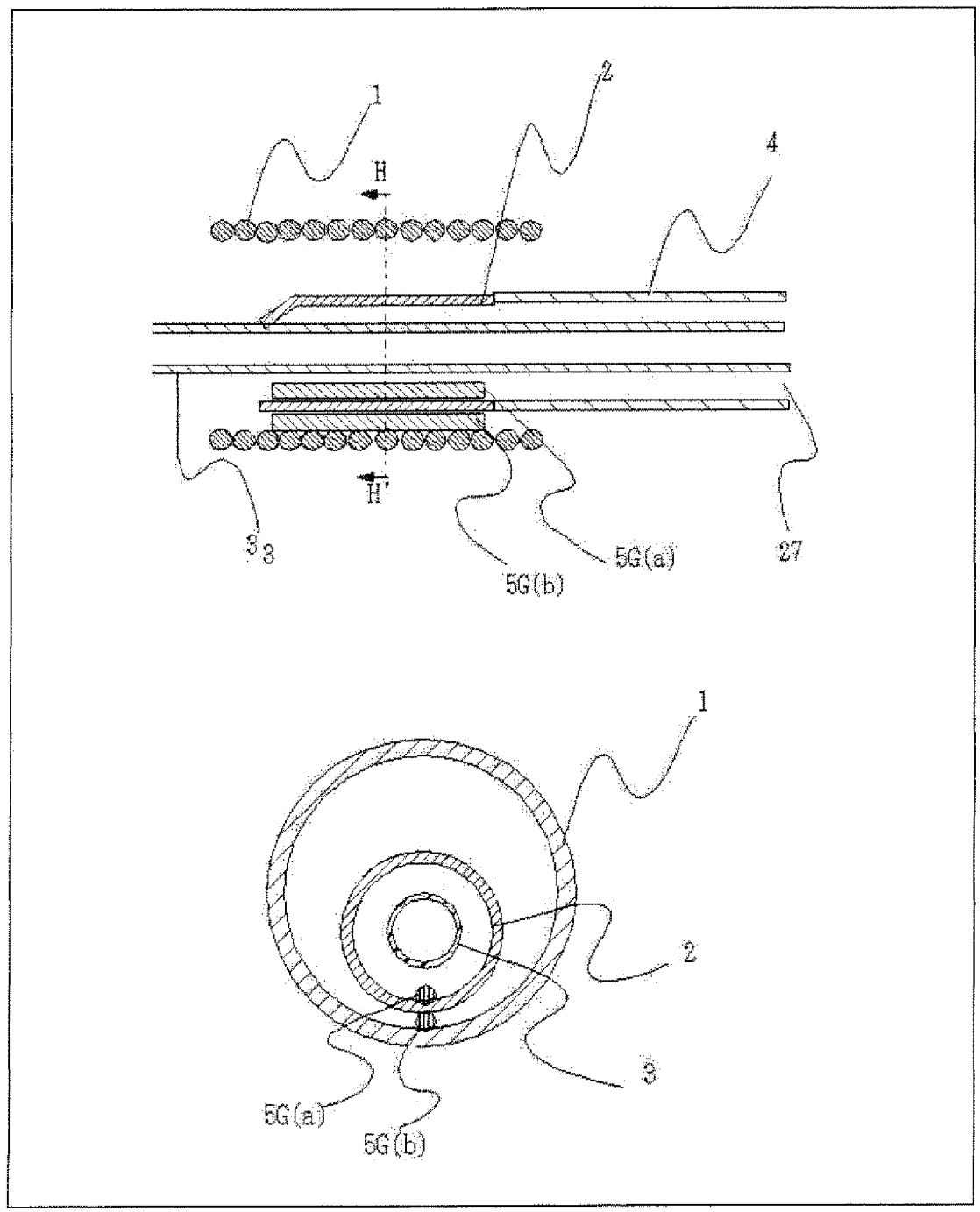
FIG. 10 illustrates (i) a cross-sectional view of a movable part of a catheter according to an eighth embodiment of the present invention, taken along the long axis direction of the catheter and (ii) a cross-sectional view taken along the plane H-H' in the short axis direction of the catheter.
Figure 11:
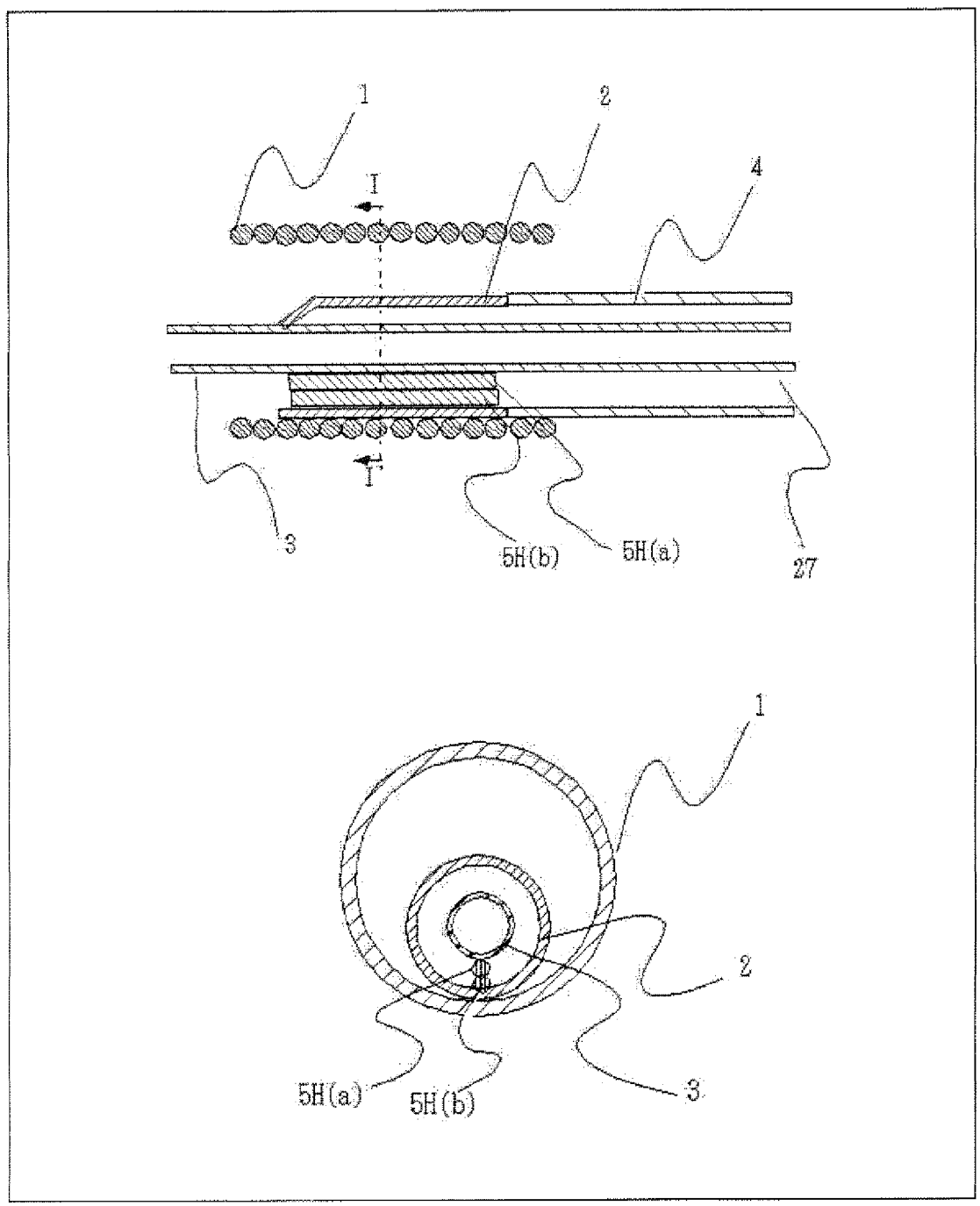
FIG. 11 illustrates (i) a cross-sectional view of a movable part of a catheter according to a ninth embodiment of the present invention, taken along the long axis direction of the catheter and (ii) a cross-sectional view taken along the plane I-I' in the short axis direction of the catheter.
Figure 12:
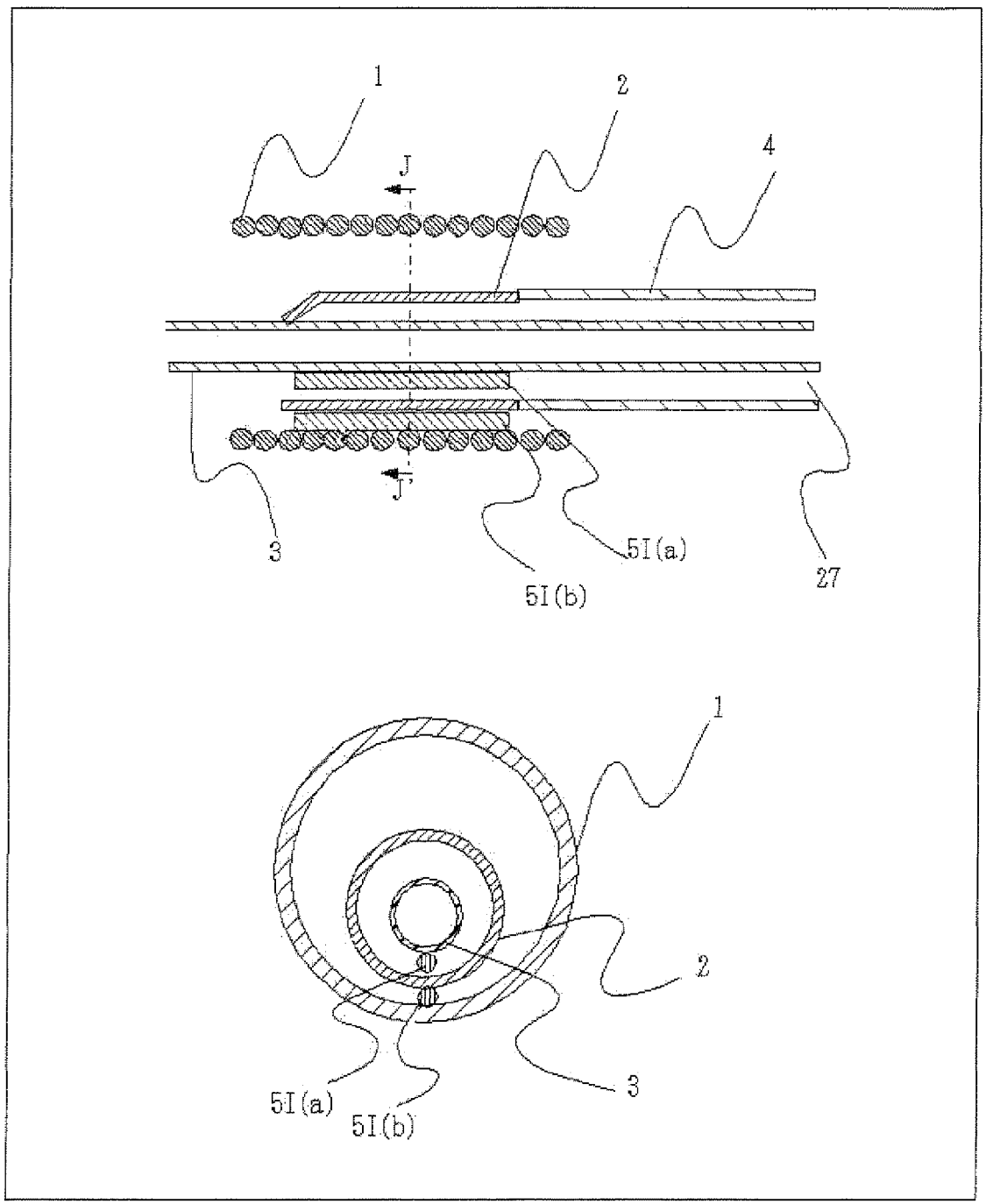
FIG. 12 illustrates (i) a cross-sectional view of a movable part of a catheter according to a tenth embodiment of the present invention, taken along the long axis direction of the catheter and (ii) a cross-sectional view taken along the plane J-J' in the short axis direction of the catheter.

It is more preferable that an intermediate member 5A be additionally provided to the above configuration (see FIG. 4). The intermediate member 5A is preferably provided so that the intermediate member 5A extends over an entire length of the restricting member 1. It is more preferable that the number of the intermediate member be plural, as illustrated in FIG. 7.

According to this configuration, the neutral surface 7 is positioned closer to the one side of the restricting member 1. This makes it possible to further reduce the percentage of the areas of the regions 9A and 9B not contributing bending, with respect to the total area of the balloon 2 (for example, see FIG. 15). As described above, according to the cross-sectional view taken along the short axis direction of the catheter, the neutral surface 7 is positioned closer to the one side of the restricting member 1. This makes it possible to increase the percentage of the area of the region 8 contributing to bending, with respect to the total area of the balloon 2. As such, the movable part 22 can be easily bent. Further, the movable part 22 thus bent is firmly kept in this shape.

[2. Restricting Member]

The restricting member 1 can have a variety of structures. For example, the restricting member 1 preferably has a braided structure, a cylindrical tube structure having notches thereon, or the like structure. A particularly preferable structure is a coil structure. This is because the restricting member 1 having the coil structure is easy to produce.

The restricting member 1 can be made of any material provided that the material is capable of restricting the inflation of the balloon 2 in the short axis direction. Examples of applicable materials encompass: metal such as SUS304 or Nitinol; radiopaque metal such as platinum; and resin having high hardness such as polyimide. Particularly preferable among the above materials is SUS304, because SUS304 is available at low price and has moderate rigidity. Further, the radiopaque metal such as platinum is also preferable because it is visually recognizable easily under radiographic visualization.

In a case of employing the restricting member 1 having the coil structure, a wire constituting the coil can have a cross-sectional surface of any shape. However, it is preferable to employ a wire having a circular cross-sectional surface, because such a wire can be easily extended in the long axis direction of the catheter.

The wire constituting the coil can have any diameter, provided that the wire has enough strength for restricting the inflation of the balloon 2 in the short axis direction of the catheter. For example, in a case of using a wire that is made of SUS304 and has the circular cross-sectional surface, the diameter of the wire is preferably 20 μm to 120 μm. Such a wire having a diameter falling within a range of 20 μm to 120 μm has flexibility, and is capable of restricting the inflation of the balloon 2 in the short axis direction of the catheter. Further, the wire makes it possible to restrict increase in an outer diameter of the coil.

Hereinafter, an interval between wires of the coil is referred to as a pitch of the coil. The pitch of the coil is not particularly limited, but a smaller pitch is more preferable. The coil having a smaller pitch can reduce the likelihood of the balloon 2 sticking out from between wires of the coil. In addition, such a coil allows the balloon 2 to efficiently extend in the long axis direction of the catheter. Furthermore, the coil having a pitch closer to 0 mm (close coiling) is more preferable. Such a coil has a smoother outer surface, and thus the catheter including the coil can be easily inserted into a blood vessel or a guide catheter. The pitch does not have to be constant over an entire length of the coil.

The outer surface of the restricting member 1 is preferably coated with a hydrophilic material so that the catheter is easily inserted into the blood vessel or the guide catheter. That is, it is preferable that a region, of the restricting member 1, which makes contact with blood, be at least partially coated with the hydrophilic material. The hydrophilic material exhibits lubricity when it makes contact with blood. Which region and how much of the binding material 1 is coated with the hydrophilic material can be determined depending on the intended use of the catheter.

The present invention can be effective regardless of which kind of hydrophilic material is used for the coating. An example of a suitable hydrophilic material is a hydrophilic polymer, such as poly(2-hydroxyethil methacrylate), polyacrylamide, or polyvinyl pyrrolidone. A method of coating the restricting member 1 with the hydrophilic material is not particularly limited either. Alternatively, the outer surface of the restricting member 1 can be covered with a thin tube so that the catheter is easily inserted into the blood vessel or the guide catheter. Which part and how much of the restricting member 1 is covered with the thin tube can be determined depending on the intended use of the catheter. The present invention can be effective regardless of which kind of thin tube is used. An example of a suitable material is a polymer such as urethane, silicon, or a styrene-isobutylene-styrene copolymer (hereinafter referred to as SIBS). A method of forming the thin tube is not limited either. Further, a shape of the thin tube can be in a shape of concertina, a notched shape, or the like. The thin tube having the concertina shape, the notched shape, or the like shape is not particularly limited as to more specific structure.

Figure 16:
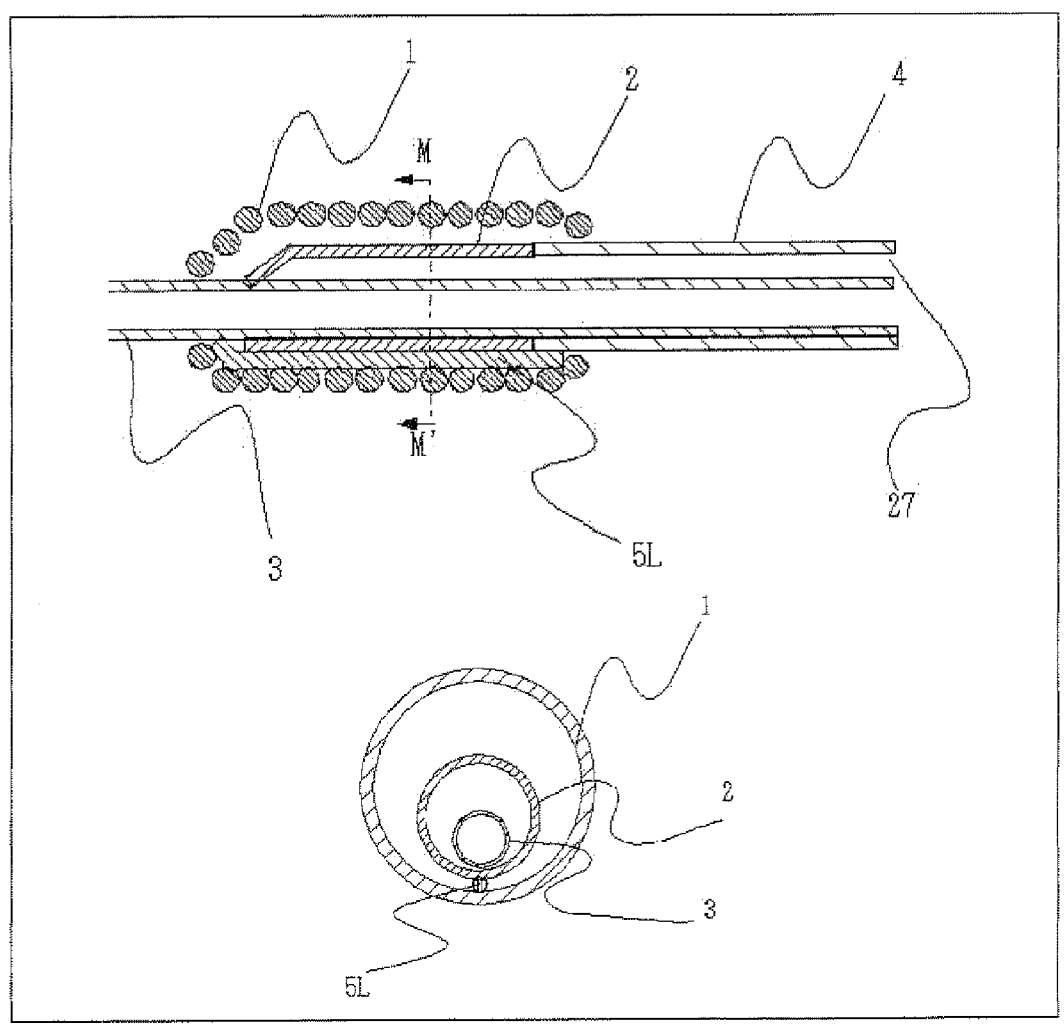
FIG. 16 illustrates (i) a cross-sectional view of a movable part of a catheter according to a thirteenth embodiment of the present invention, taken along the long axis direction of the catheter and (ii) a cross-sectional view taken along the plane M-M' in the short axis direction of the catheter.

The restricting member 1 is provided for restricting the balloon 2 inflating in the short axis direction of the catheter. However, in this configuration, there is a likelihood that the balloon 2 sticks out of one or both ends of the restricting member 1. Therefore, the both ends of the restricting member 1 are preferably sealed. A method of sealing the both ends of the restricting member 1 is not particularly limited. An example is, as illustrated in FIG. 16, the restricting member 1 is tapered toward one end so that the one end is attached to the tube 3. Thus, the balloon 2 can be prevented from sticking out of one or both ends of the restricting member 1 even when the balloon 2 is extended in the long axis direction of the catheter. Alternatively, the both ends of the restricting member 1 can be sealed by using resin such as an urethane adhesive, a polyimide film, silicon, or SIBS.

[3. Balloon]

Figure 13:
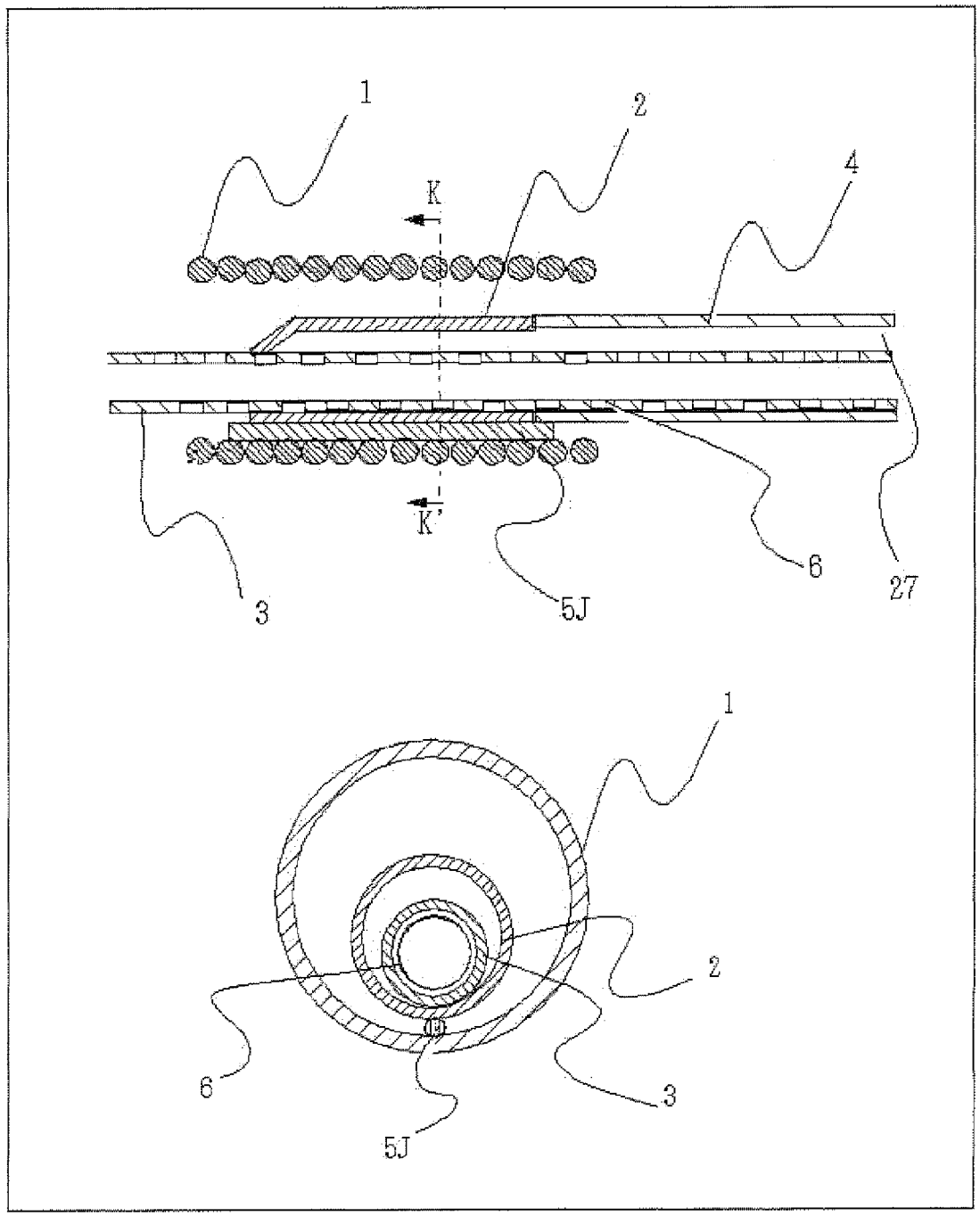
FIG. 13 illustrates (i) a cross-sectional view of a movable part of a catheter according to an eleventh embodiment of the present invention, taken along the long axis direction of the catheter and (ii) a cross-sectional view taken along the plane K-K' in the short axis direction of the catheter.
Figure 14:
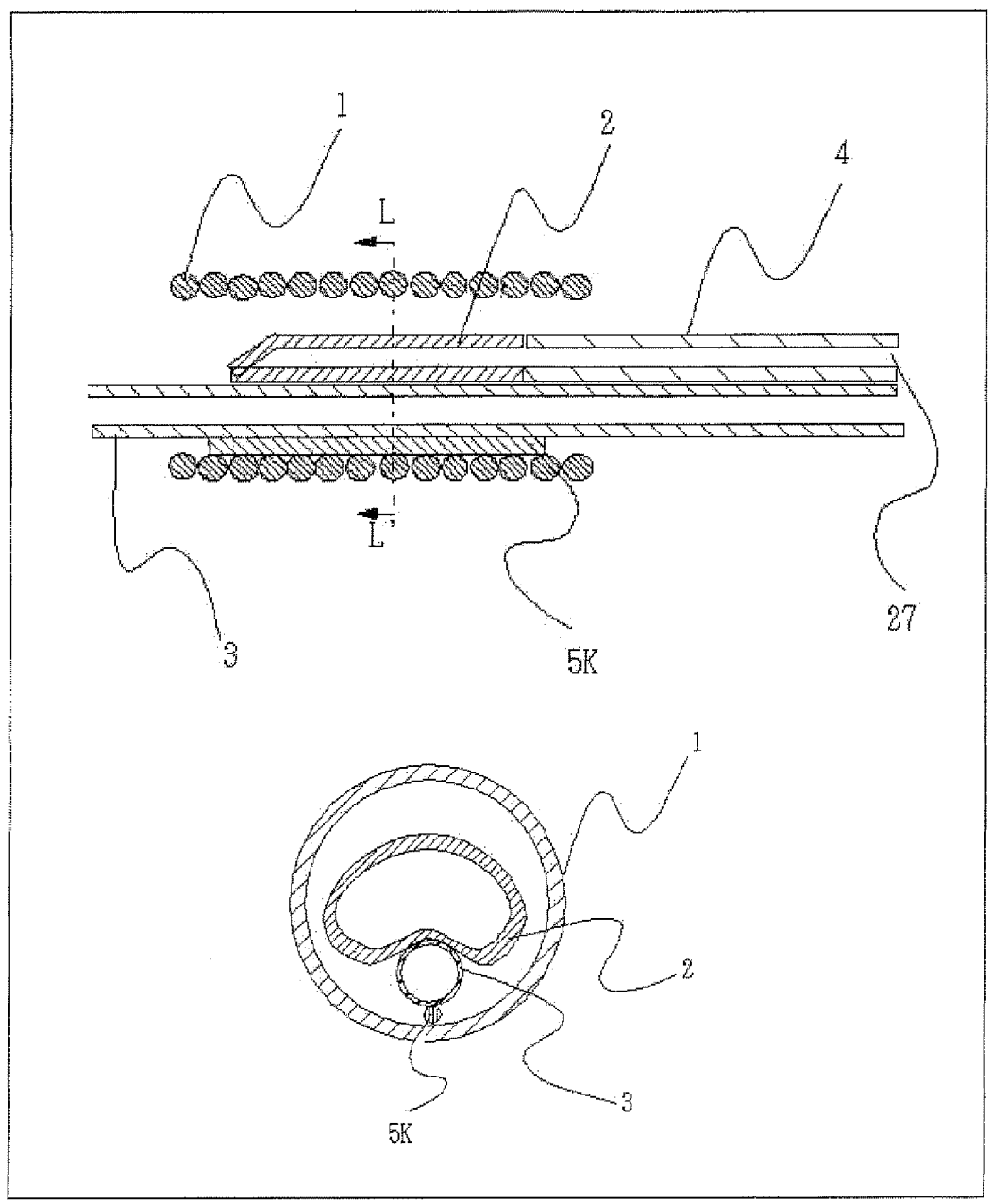
FIG. 14 illustrates (i) a cross-sectional view of a movable part of a catheter according to a twelfth embodiment of the present invention, taken along the long axis direction of the catheter and (ii) a cross-sectional view taken along the plane L-L' in the short axis direction of the catheter.

As illustrated in FIGS. 3 through 14, the balloon 2 is provided near the distal end of the tube 3 and outside the outer surface of the tube 3. A shape of the balloon 2 is not particularly limited. However, the balloon 2 is preferably in a tubular shape, because such a tubular balloon 2 is easy to produce. In a case of the configuration as illustrated in FIGS. 3 through 13, the distal end of the balloon 2 is attached to the outer surface of the tube 3, while the proximal end of the balloon 2 is attached to the outer surface of the tube 3 or to the outer shaft 4. A method of attaching the balloon 2 to the tube 3 or to the outer shaft 4 is not particularly limited. It is preferable to employ pressure bonding, adhesive bonding, welding, or the like. In a case where a clearance between the balloon 2 and the tube 3 is so large that it is difficult to attach the balloon 2 to the tube 3, the balloon 2 can be tapered toward the both ends. In a case of the configuration as illustrated in FIG. 14, the both ends of the balloon 2 can be sealed by any method. For example, both ends of the balloon 2 can be sealed by bonding the balloon 2 to the tube 3 by pressure-bonding or by adhesive-bonding. Alternatively, the both ends of the balloon 2 can be sealed by using resin such as urethane, silicon, polyamide elastomer, or SIBS resin.

A material constituting the balloon 2 is not particularly limited, and can be determined depending on the intended use of the catheter. For example, the balloon 2 is preferably made of resin such as polyurethane, silicon, SIBS, or polyamide elastomer resin. For example, the description is given below as to a microcatheter. In order to use the catheter inside a peripheral blood vessel having many sharp curves, it is necessary that the movable part 22 of the catheter be sharply bent with a small curvature. In addition, a rigid guide wire may be inserted into a lumen of the tube 3. Therefore, the movable part 22 should be capable of keeping its bended shape firmly against the rigidity of the guide wire. To this end, the balloon 2 is required to be extendable sufficiently in the long axis direction of the catheter, and have high pressure tolerance. For this reason, it is preferable to employ a flexible, high pressure-tolerant material such as urethane or polyamide elastomer.

A wall thickness of the balloon 2 is not particularly limited, and can be determined as appropriate depending on the use of the catheter. For example, in a case where the balloon 2 is made of urethane and is employed in the microcatheter, the balloon 2 preferably has a wall thickness with which flexibility and high pressure tolerance of urethane can be achieved. Specifically, the wall thickness of the balloon 2 is preferably 20 µm to 300 µm. Further, in order to prevent the outer diameter of the catheter 21 from increasing, the wall thickness of the balloon 2 is more preferably 20 µm to 150 µm.

A size of the balloon 2 is not particularly limited, and can be determined as appropriate depending on the intended use of the catheter. For example, the description is given as to the balloon 2 being employed in the microcatheter. In order to freely operate the microcatheter inside a blood vessel, it is preferable that the outer diameter of the balloon 2 be 0.2 mm to 3 mm. Further, a length of the balloon 2 in the long axis direction of the catheter is preferably 0.5 mm to 10.0 mm.

A production method of the balloon 2 is not particularly limited. In order to produce the balloon 2, which can be expanded and contracted by adjusting inner pressure, it is possible to employ dip molding, blow molding, an evaporation method, or the like method. The production method of the balloon 2 can be selected from those listed above as appropriate depending on the intended use of the catheter. In a case where the balloon 2 has to keep its shape more firmly once it is bent, it is preferable to employ the blow molding. The blow molding makes it possible to produce the balloon 2 having sufficient pressure tolerance. An example of the production method, employing the blow molding, of the balloon 2 is described below. First, a tubular parison of a predetermined size is made by using extrusion molding etc. Next, the tubular parison is put in a mold having an intended shape of the balloon. Then, the tubular parison is extended both in an axis direction and in a radial direction through a biaxial pulling process, so as to obtain a balloon having a shape identical to the shape of the mold. The biaxial pulling process may be performed under heating, and may be performed plural number of times. Further, the pulling in the axis direction may be performed concurrently with the pulling in the radial direction, and may be performed before or after the pulling in the radial direction. Furthermore, an annealing treatment may be additionally carried out so as to gain stability of the shape and size of the balloon 2.

A type of resin constituting the tubular parison is not particularly limited. For example, it is preferable to employ resin such as polyolefin, polyester, polyamide, or polyurethane. It is more preferable to employ (i) resin obtained by blending two or more types of resin selected from those listed above or (ii) a material having a multilayer structure obtained by stacking two or more types of resin selected from those listed above.

Further, the balloon 2 preferably includes a valve in case the balloon 2 allowed air to be leaked in. The valve makes it possible to easily remove the air from the balloon 2. A configuration of the valve is not particularly limited provided that the valve has a valvular function. For example, a one-way valve or the like can be attached to the balloon 2 at the distal end of the balloon 2.

[4. Tube]

The tube 3 may be provided so that the tube 3 extends over the entire catheter 21 (e.g., the OTW type catheter as illustrated in FIG. 1). Alternatively, the tube 3 can be provided so that the proximal end aperture of the tube 3 is positioned in the middle of the outer shaft 4 (e.g., the RX type catheter as illustrated in FIG. 2). The tube 3 is preferably made of a single member for ease of production. However, for example in a case where the catheter 21 needs to have rigidities that are different for each part of the catheter 21, and if the different rigidities of the catheter 21 should be achieved by the tube 3, then the tube 3 can be made of a plurality of members joined with each other in the middle of the catheter 21.

The tube 3 has a lumen through which the guide wire, a medical solution, or the like can pass. The tube 3 preferably has a uniform inner diameter for ease of production. However, for example in order to obtain a catheter that can be more easily inserted so that the distal end thereof is positioned beyond a CTO lesion, it is preferable that the tube 3 have an outer diameter and an inner diameter which gradually decrease toward the distal end of the catheter 1.

The tube 3 can be made of a variety of materials. Among the variety of materials, it is particularly preferable to employ resin for ease of production. Examples of suitably applicable resin are polyolefin, polyamide, polyurethane, polyimide, polyethylene, polytetrafluoroethylene (PTFE), and the like.

The tube 3 is preferably made of a material which exhibits good chemical resistance, good antithrombogenicity, and good slidability against the guide wire. Such a material is for example fluorine resin or high-density polyethylene. In a case of employing a material whose inner layer does not have a desired characteristic such as antithrombogenicity, the tube 3 can be coated so that a resultant tube 3 has an inner layer having the desired characteristic.

Further, the tube 3 can have at least partially multi-layered structure. In this case, an innermost layer of the tube 3 is preferably made of a resin material such as PTFE or high-density polyethylene, while an outermost layer of the tube 3 is preferably made of a resin material such as polyamide, polyurethane, or SIBS. According to this configuration, the tube 3 can gain flexibility. It is more preferable that the tube 3 be made of a material that can be fused with the balloon 2.

In the case where the tube 3 has at least partially multi-layered structure, the tube 3 preferably has a reinforcing layer 6 between the innermost layer and the outermost layer (e.g., in the middle of the innermost and outermost layers) (FIG. 13 illustrates an exemplary catheter including the tube 3 having the reinforcing layer 6). Provision of the reinforcing layer 6 makes it possible to improve kink resistance.

A material constituting the reinforcing layer 6 is not particularly limited provided that the material exhibits the kink resistance. Examples of the material suitably applicable for the reinforcing layer 6 are for example a metal coil, a braided metal, a metal core wire, and the like materials.

[5. Intermediate Member]

It is important for intermediate members 5A through 5L to have stretchability relatively lower than that of the balloon 2, in the long axis direction of the catheter. It is particularly preferable that the intermediate members 5A through 5L have no stretchability in the long axis direction of the catheter.

A material constituting the intermediate members 5A through 5L is not limited to a particular kind provided that the material exhibits the above characteristic. Examples of suitably applicable material are for example: metal such as SUS304, Nitinol, or platinum; an adhesive such as that made of urethane or cyanoacrylate; or fiber resin such as nylon or Beckley.

A shape of the intermediate members 5A through 5L, is not limited to a particular kind. For example, the intermediate members 5A through 5L preferably have a cylindrical shape or a columnar shape.

FIG. 4 illustrates a catheter in which the intermediate member 5A having no stretchability in the long axis direction of the catheter is in contact with the restricting member 1. The intermediate member 5A can have any structure. Particularly, the intermediate member 5A is preferably structured such that the intermediate member 5A is in contact with an entire length of the restricting member 1. This is because this structure prevents the intermediate member 5A from being slack when the movable part 22 of the catheter is bent. Further, the above structure makes it possible to surely bend the movable part 22 in a desired direction. The intermediate member 5A provides a sufficient effect when at least both ends of the intermediate member 5A are fixed to the both ends of the restricting member 1. However, the intermediate member 5A is preferably fixed to the restricting member 1 over an entire length of the intermediate member 5A. A method of fixing the intermediate member 5A to the restricting member 1 is not particularly limited provided that the fixation is achieved. For example, it is possible to employ adhesive bonding or welding.

The intermediate member 5A is provided on a side on which the tube 3 is eccentrically provided. Particularly, the intermediate member 5A is preferably provided as close as possible to a side toward which the movable part 22 is to be bent (the one side). According to this configuration, the neutral surface 7 is positioned closer to the one side of the restricting member 1. This makes it possible to reduce the percentage of the areas of the regions not contributing to bending, with respect to the total area of the balloon 2 (for example, see FIG. 15). As described above, according to the cross-sectional view taken along the short axis direction of the catheter, the neutral surface 7 is positioned near the one side of the restricting member 1. This makes it possible to increase the percentage of the area of the region contributing to bending, which region exists on a side opposite to the one side of the restricting member 1, with respect to the total area of the balloon 2. As such, the movable part 22 can be efficiently and easily bent by low fluid pressure. Further, the movable part 22 thus bent is firmly kept in this shape by increasing the fluid pressure. Furthermore, it becomes possible to easily produce the catheter.

Figure 5:
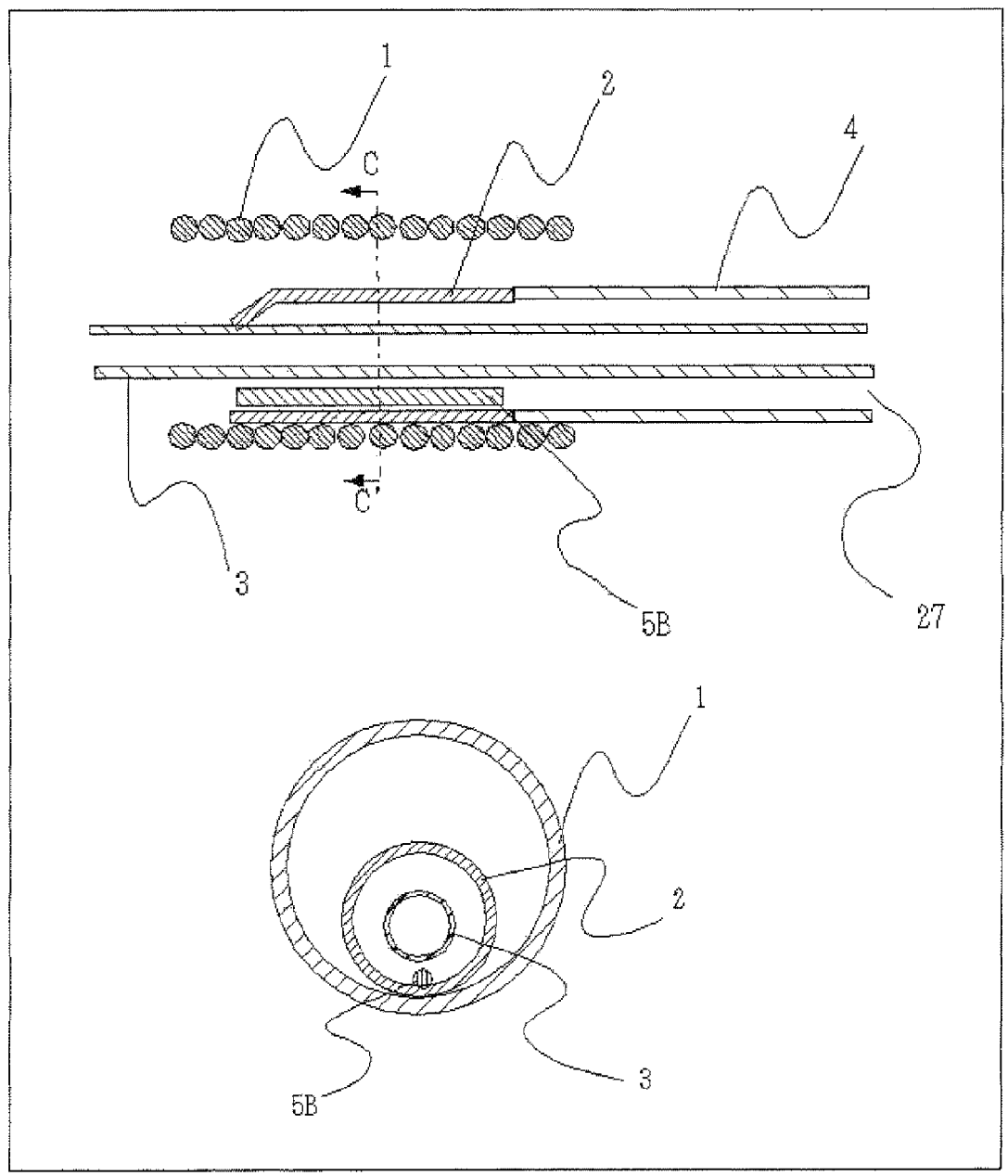
FIG. 5 illustrates (i) a cross-sectional view of a movable part of a catheter according to a third embodiment of the present invention, taken along the long axis direction of the catheter and (ii) a cross-sectional view taken along the plane C-C' in the short axis direction of the catheter.

FIG. 5 illustrates a catheter in which the intermediate member 5B having no stretchability in the long axis direction of the catheter is provided between the restricting member 1 and the tube 3. The intermediate member 5B can have any structure. Particularly, the intermediate member 5B is preferably provided between the restricting member 1 and the tube 3 so that the intermediate member 5B is in parallel with the long axis direction of the catheter over the entire length of the restricting member 1. This structure is preferable because it prevents the intermediate member 5B from being slack when the movable part 22 of the catheter is bent. Further, the structure makes it possible to surely bend the movable part 22 in the desired direction. A method of fixing the intermediate member 5B to the restricting member 1 is not particularly limited provided that the fixation is achieved. For example, it is possible to employ adhesive bonding or welding.

The intermediate member 5B is provided on the side on which the tube 3 is eccentrically provided. Particularly, the intermediate member 5B is preferably provided as close as possible to the side toward which the movable part 22 is to be bent (the one side). According to this configuration, the neutral surface 7 is positioned closer to the one side of the restricting member 1. This makes it possible to reduce the percentage of the areas of the regions not contributing to bending, with respect to the total area of the balloon 2 (for example, see FIG. 15). As described above, according to the cross-sectional view taken along the short axis direction of the catheter, the neutral surface 7 is positioned near the one side of the restricting member 1. This makes it possible to increase the percentage of the area of the region contributing to bending, which region exists on the side opposite to the one side of the restricting member 1, with respect to the total area of the balloon 2. As such, the movable part can be efficiently and easily bent by low fluid pressure. Further, the movable part 22 thus bent is firmly kept in this shape by increasing the fluid pressure. Furthermore, it becomes possible to easily produce the catheter.

Figure 6:
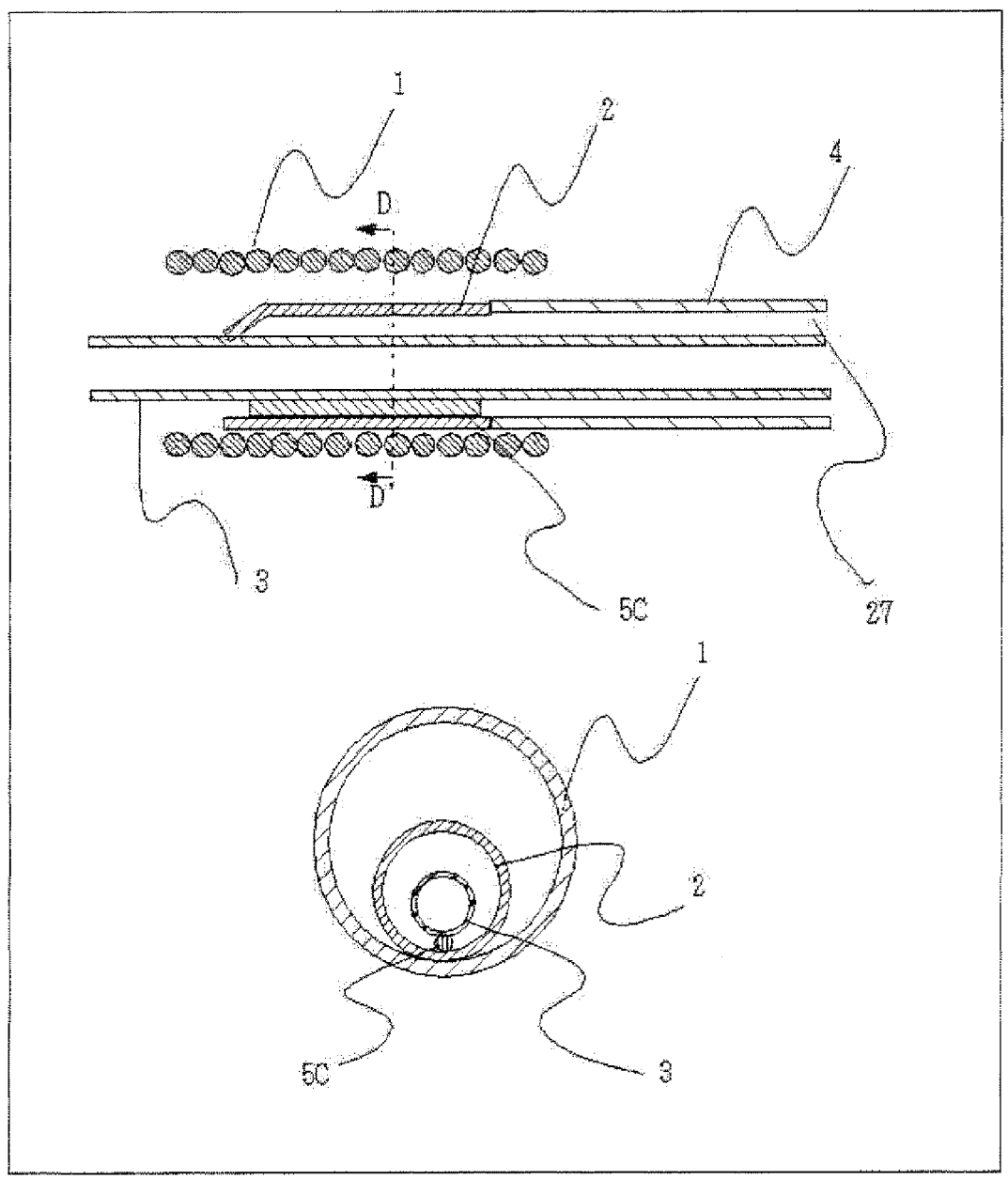
FIG. 6 illustrates (i) a cross-sectional view of a movable part of a catheter according to a fourth embodiment of the present invention, taken along the long axis direction of the catheter and (ii) a cross-sectional view taken along the plane D-D' in the short axis direction of the catheter.

FIG. 6 illustrates a catheter in which the intermediate member 5C having no stretchability in the long axis direction of the catheter is in contact with the tube 3. The intermediate member 5C can have any structure. Particularly, the intermediate member 5C is preferably provided in parallel with the long axis direction of the catheter over the entire length of the restricting member 1. This structure is preferable because it prevents the intermediate member 5C from being slack when the movable part 22 of the catheter is bent. Further, the structure makes it possible to surely bend the movable part 22 in the desired direction. The intermediate member 5C provides a sufficient effect when at least both ends of the intermediate member 5C are fixed to the tube 3. However, the intermediate member 5C is preferably fixed to the tube 3 over the entire length of the intermediate member 5C. A method of fixing the intermediate member 5C to the tube 3 is not particularly limited provided that the fixation is achieved. For example, it is possible to employ adhesive bonding or welding.

The intermediate member 5C is provided on the side on which the tube 3 is eccentrically provided. Particularly, the intermediate member 5C is preferably provided as close as possible to the side to which the movable part 22 is to be bent (the one side). According to this configuration, the neutral surface is positioned closer to the one side of the restricting member 1. This makes it possible to reduce the percentage of the areas of the regions not contributing to bending, with respect to the total area of the balloon 2 (for example, see FIG. 15). As described above, according to the cross-sectional view taken along the short axis direction of the catheter, the neutral surface is positioned near the one side of the restricting member 1. This makes it possible to increase the percentage of the area of the region contributing to bending, which region exists on the side opposite to the one side of the restricting member 1, with respect to the total area of the balloon 2. As such, the movable part can be efficiently and easily bent by low fluid pressure. Further, the movable part 22 thus bent is firmly kept in this shape by increasing the fluid pressure. Furthermore, it becomes possible to easily produce the catheter.

FIGS. 7 through 12 respectively illustrate catheters in which the intermediate members 5D(a) through 5I(b) having no stretchability in the long axis direction of the catheter are provided. The intermediate members 5D(a) through 5I(b) can have any structure, but each of the intermediate members 5D(a) through 5I(b) is preferably provided in parallel with the long axis direction of the catheter over the entire length of the restricting member 1. This configuration is preferable because it prevents the intermediate members 5D(a) through 5I(b) from being slack when the movable part 22 of the catheter is bent. Further, the structure makes it possible to surely bend the movable part 22 in the desired direction. The intermediate members 5D(a) through 5I(b) provide a sufficient effect when at least both ends of each of the intermediate members 5D(a) through 5I(b) are fixed to the both ends of the restricting member 1. However, each of the intermediate members 5D(a) through 5I(b) is preferably fixed to the restricting member 1 over the entire length of the each of the intermediate members 5D(a) through 5I(b). A method of fixing each of the intermediate members 5D(a) through 5I(b) to the restricting member 1 is not particularly limited provided that the fixation is achieved. For example, it is possible to employ adhesive bonding or welding.

Each of the intermediate members 5D(a) through 5I(b) is provided on the side on which the tube 3 is eccentrically provided. Particularly, each of the intermediate members 5D(a) through 5I(b) is preferably provided as close as possible to the side to which the movable part 22 is to be bent (the one side). According to this configuration, the neutral surface is positioned closer to the one side of the restricting member 1. This makes it possible to reduce the percentage of the areas of the regions not contributing to bending, with respect to the total area of the balloon 2 (for example, see FIG. 15). As described above, according to the cross-sectional view taken along the short axis direction of the catheter, the neutral surface is positioned near the one side of the restricting member 1. This makes it possible to increase the percentage of the area of the region contributing to bending, which region exists on the side opposite to the one side of the restricting member 1, with respect to the total area of the balloon 2. As such, the movable part 22 can be efficiently and easily bent by low fluid pressure. Further, the movable part 22 thus bent is firmly kept in this shape by increasing the fluid pressure. Furthermore, it becomes possible to easily produce the catheter.

[6. Outer Shaft]

A material constituting the outer shaft 4 is not particularly limited provided that the material can secure a lumen which allows the pressure fluid to flow toward the balloon 2. In view of workability, biosafety, and the like, examples of suitable and preferable material are metal such as SUS304 and a high-rigidity resin material such as polyimide or polyamide. The outer shaft 4 is provided coaxially with the tube 3 so that an inner surface of the outer shaft 4 and an outer surface of the tube 3 define a pressure fluid lumen. Alternatively, it is possible to additionally provide a pressure fluid tube in parallel with the tube 3 inside the outer shaft 4. The outer shaft 4, the tube 3, and the pressure fluid tube form a biaxial structure. Further, the pressure fluid tube has an inner surface serving as the pressure fluid lumen.

The outer shaft 4 is preferably made of a single member for ease of production. However, for example in a case where the catheter 21 needs to have rigidities that are different for each part of the catheter, and if the different rigidities of the catheter 21 should be achieved by the outer shaft 4, then the outer shaft 4 can be made of a plurality of members joined with each other in the middle of the catheter 21.

[7. Coating]

The outer surface of the catheter 21 is preferably at least partially coated with the hydrophilic material so that the catheter 21 is easily inserted into the blood vessel or the guide catheter. Which part and how much of the outer surface of the catheter 21 is coated with the hydrophilic material can be determined depending on the intended use of the catheter 21. The present invention is effective regardless of which kind of the hydrophilic material is used. An example of the suitable hydrophilic material is a hydrophilic polymer, such as poly (2-hydroxyethil methacrylate), polyacrylamide, or polyvinyl pyrrolidone. A method of coating the outer surface of the catheter 21 with the hydrophilic material is not particularly limited either.

[8. Radiopaque Marker]

It is preferable that the catheter 21 include a radiopaque marker near the distal end aperture of the catheter 21. According to the configuration, it is possible to know, by using X-ray, where the distal end of the catheter 21 is positioned. Accordingly, it is possible to easily operate the catheter for example within a living body. A material constituting the radiopaque marker is not particularly limited provided that the material is substantially radiopaque. Examples of such a material are metal and resin. The radiopaque marker may contain only one marker. Alternatively, the radiopaque marker may contain two or more markers. The radiopaque marker may be attached to the tube 3. Such a radiopaque marker is easy to produce. A marker 33 can be in any shape, but it is preferable that the marker 33 be in a form of hollow ring. The marker 33 in the form of hollow ring is easy to visualize, because such a marker 33 looks an identical shape as seen from any radial direction of the catheter 1. Further, such a radiopaque marker is easy to produce.

Alternatively, it is possible to employ a restricting member 1 made of a radiopaque material. This makes it possible to obtain a catheter having a flexible distal end. In addition, such a radiopaque marker is easy to produce.

[9. Hub]

It is preferable that the outer shaft 4 include a hub 23 at its proximal end. A material constituting the hub 21 is not particularly limited. A suitably applicable material is for example resin such as polycarbonate, polyamide, polyurethane, polysulphone, polyarylate, styrene-butadiene copolymer, or polyolefin.

A method of joining the hub 23 to the outer shaft 4 is not particularly limited, and can be selected from commonly known methods. For example, the hub 23 and the outer shaft 4 can be joined together by using an adhesive. In a case where the hub 23 and the outer shaft 4 are made of a material that can be fusion-bonded, it is possible to employ for example fusion bonding. The adhesive to be used is not limited as to its composition, chemical construction, and curing manner. Specifically, in view of the composition and chemical construction, it is preferable to employ an urethane type adhesive, silicon type adhesive, epoxy type adhesive, cyanoacrylate type adhesive, or the like adhesive. On the other hand, in view of the curing manner, it is preferable to employ a two-component adhesive, UV-curing adhesive, water absorption curing adhesive, heat-curing adhesive, or the like adhesive. The adhesive to be used preferably has hardness, after being cured, so that the hardness of the adhesive is substantially the same as those of the hub 23 and the outer shaft 4 at a joining area. To this end, it is preferable to select the adhesive in consideration of the materials constituting the hub 23 and the outer shaft 4 at the joining area, sizes of the hub 23 and the outer shaft 4 at the joining area, rigidities of the hub 23 and the outer shaft 4 at the joining area, and the like. Further, in order to achieve a joining area having a small diameter, it is preferable to heat-treat the joining area. In a case where the hub 23 and/or the outer shaft 4 at the joining area is made of a poorly-adherent material such as polyolefin, the joining area is preferably plasma-treated by using oxygen gas or the like so as to enhance adhesiveness before the hub 23 and the outer shaft 4 are joined together by using the adhesive.

[10. Exemplary Function of Catheter]

Each of the above catheters can be either of two types of catheters, which are distinguished according to the length of a guidewire lumen. The description is given below as to a general catheter.

One of the two types of catheters is an over-the-wire (OTW) type catheter, in which the tube 3 extends over an entire length of the catheter 21 from the distal end aperture 26 to the proximal end aperture 24 on the hub 23 (see FIG. 1). The other one of the two types of catheters is a rapid exchange (RX) type catheter, in which the guide wire lumen extends from the distal end of the microcatheter to the middle of the microcatheter, and the proximal end aperture 24 of the tube 3 is provided in the middle of the outer shaft 4 (see FIG. 2).

The OTW type catheter has the guide wire lumen extending over the entire length of a balloon catheter. Therefore, the OTW type catheter is usually used as a backup catheter. The backup catheter guides the guide wire so that a distal end of the guide wire is positioned beyond a lesion that is difficult for the guide wire to pass through. On the other hand, the RX type catheter can be easily removed from a lesion site while leaving the guide wire in the lesion site. Therefore, the RX type catheter may be used for this purpose.

Figure 17:
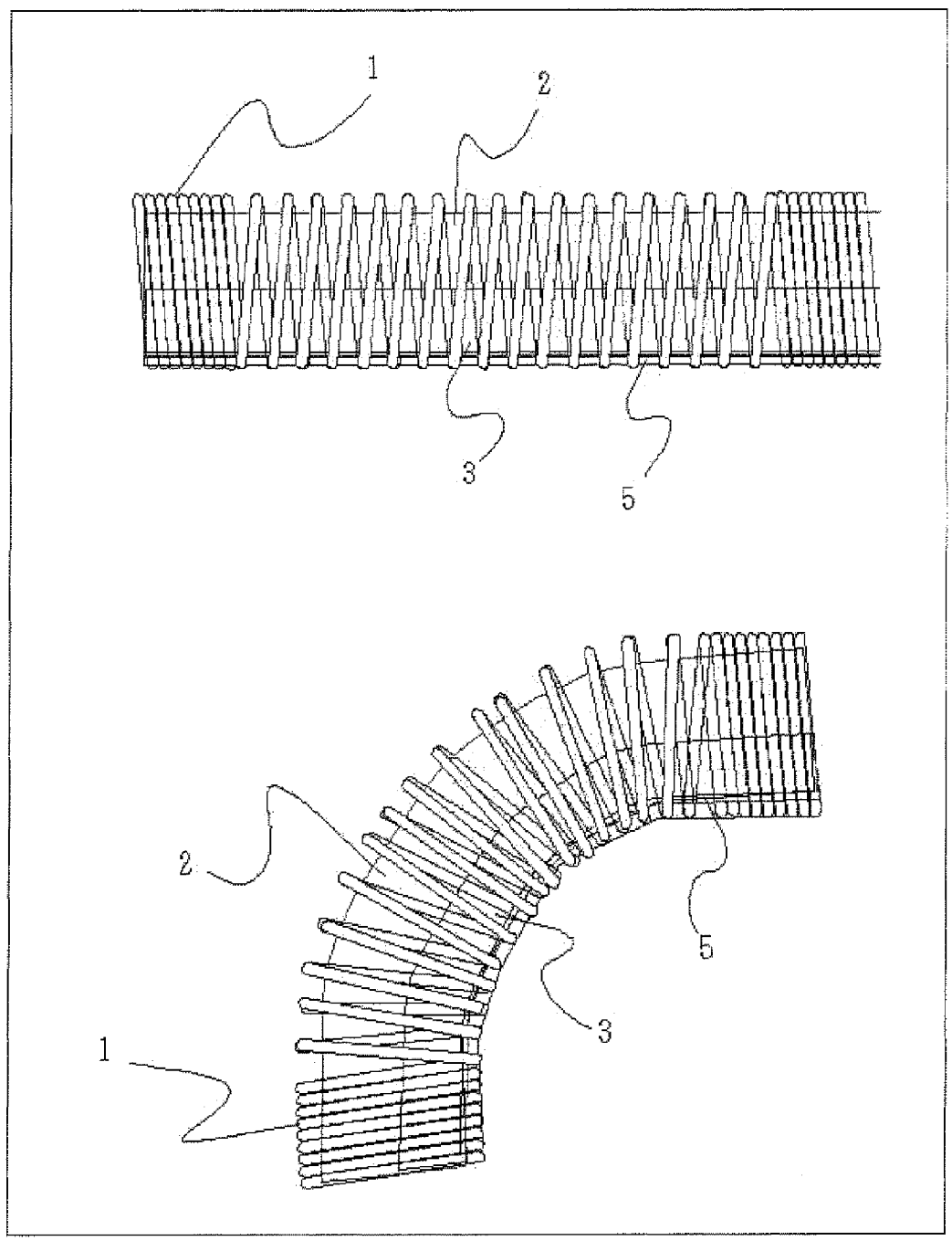
FIG. 17 schematically illustrates a movable part 22, in a bent state, of the catheter according to the embodiment of the present invention.

FIG. 17 illustrates a movable part 22, which is in a straight state and in a bent state, of a catheter according to the embodiment of the present invention.

The movable part 22 is bent through the following steps. First, the balloon is supplied with liquid such as physiological saline or radiopaque dye. Next, the hub 23 is connected with an indeflator, syringe, or the like. Then, the indeflator, syringe, or the like connected as above supplies fluid to the balloon. The movable part 23 is thus bent in a desired way based on a relationship between pressure and a bending angle and/or a relationship between flow volume and the bending angle. In performing these steps, if necessary, it is possible to completely let out immixed air via a valve attached to the distal end of the balloon 2. Thereafter, the guide wire, medical solution, or the like is inserted into the tube 3 so as to treat the lesion site by using the balloon catheter or the like. The movable part 22 of the catheter inflated as above can restore its original shape by restoring the pressure, flow volume, or the like changed by the indeflator, syringe, or the like.

EXAMPLES

Specific examples of the present invention are described below in detail. However, the present invention is not limited to the following examples.

Evaluation was carried out by (i) producing samples each including a movable part only and (ii) using the samples thus produced. The following description is given on an assumption that names of elements and reference numerals given to the elements (e.g., tube 1, tube 2) are the same as those described above with reference to the attached figures, for the sake of easy explanation for clarifying the configuration of the tube.

[Method of Producing Catheter]

Example 1

A coil 1 used here was made of SUS (made by MARUHO HATSUJYO). An outer diameter of the coil 1 was 1.7 mm. The coil 1 had a circular cross-sectional surface. A diameter of a wire constituting the coil 1 was 100 μm. A pitch of the coil 1 was 0.10 mm. A length of the coil 1 was 15 mm.

A balloon 2 was produced in the following manner. First, a solution was prepared by mixing polyurethane and methylene chloride (serving as solvent) so that the polyurethane accounted for 5% by weight of the solution. The polyurethane used here was a mixture of "Tecoflex EG-85A" (made by Thermedics, shore hardness was 77A and tensile strength was 550%) and "Tecoflex EG-93A" (made by Thermedics, shore hardness was 87A and tensile strength was 390%). The solution obtained was then used for dip molding, so as to obtain the balloon 2. The dip molding was carried out in the following manner. A mandrel which was coated with polytetrafluoroethylene and whose outer diameter was 1.5 mm was used as a core material. The core material was dipped in the above solution and then removed from the solution, so as to form a balloon tube on the mandrel. This process was repeatedly carried out until a wall thickness of the balloon tube was 70 μm. Thereafter, the balloon tube obtained was cut by a cutter so that a length of the balloon tube was 10 mm, thereby obtaining the balloon 2.

A tube 3 (inner diameter was 0.43 mm and outer diameter was 0.56 mm) was produced through extrusion molding by using polyamide ("PEBAX5533SA01", made by elf atochem). The tube 3 obtained was cut by the cutter so that a length of the tube 3 was 50 mm.

A two-component urethane adhesive was applied to one side of the tube 3 so that an adhesion margin was 10 mm long. The tube 3 was then inserted into the balloon 2 so that the adhesion margin was bonded to an inner surface of the balloon 2. A pressure fluid tube was inserted into the balloon 2 from a proximal end aperture of the balloon 2. Then, the two-component urethane adhesive was applied to an inner surface of the balloon 2 at apertures of both ends. Thereafter, the both ends of the balloon 2 were sealed by thermocompression. The two-component urethane adhesive was produced by mixing NIPPOLLAN 4235 and CORONATE 4403 (both are made by NIPPON POLYURETHANE INDUSTRY CO., LTD.) at a ratio of 2:1.

Next, the tube 3, which had the balloon 2 fixed to its outer surface, was inserted into the coil 1 so that the one side of the balloon 2 at which side the tube 3 was fixed was in contact with one side of the coil 1. Then, the coil 1 was bonded to the balloon 2 having the tube 3 inside thereof, by using the two-component urethane adhesive.

Example 2

Example 2 was carried out by using the coil 1, balloon 2, and the tube 3, which are the same as those used in Example 1. In addition to these members, an intermediate member 5A was used. The intermediate member 5A was prepared by cutting an SUS wire whose diameter was 30 µm (made by KOBELCO) so that its length was 15 mm.

The two-component urethane adhesive was applied to the one side of the tube 3 so that the adhesion margin was 10 mm long. The tube 3 was then inserted into the balloon 2 so that the adhesion margin was bonded to the inner surface of the balloon 2. The pressure fluid tube was inserted into the balloon 2 from the proximal end aperture of the balloon 2. Then, the two-component urethane adhesive was applied to the inner surface of the balloon 2 at apertures of both ends. Thereafter, the both ends of the balloon 2 were sealed by thermocompression. The two-component urethane adhesive was produced by mixing NIPPOLLAN 4235 and CORONATE 4403 (both are made by NIPPON POLYURETHANE INDUSTRY) at a ratio of 2:1.

Next, the tube 3, which had the balloon 2 fixed to its outer surface, was inserted into the coil 1 so that the one side of the balloon 2 at which side the tube 3 was fixed was in contact with the one side of the coil 1. Then, the intermediate member 5A was inserted into between the balloon 2 and the coil 1. Thereafter, the intermediate member 5A was bonded to the coil 1 by using the two-component urethane adhesive.

Then, the coil 1 was bonded to the balloon 2 having the tube 3 inside thereof.

Comparative Example 1

Comparative Example 1 was carried out in a same manner as in Example 1 except that the coil 1 was not provided.

Comparative Example 2

The tube 3, which had the balloon 2 fixed to its outer surface, was inserted into the coil 1 so that the one side of the balloon 2 at which side the tube 3 was fixed was not in contact with the one side of the coil 1. Then, the intermediate member 5A was inserted into between the balloon 2 and the coil 1. Thereafter, the intermediate member 5A was bonded to the coil 1 by using the two-component urethane adhesive.

Then, the coil 1 was bonded to the balloon 2 having the tube 3 inside thereof.

[Evaluation]

Each of pressure fluid tubes of Example 1, Example, 2, Comparative Example 1, and Comparative Example 2 was connected with an indeflator. Next, a movable part of Example 1, Example, 2, Comparative Example 1, and Comparative Example 2 was bent in warm water at 37° C. under 4 atmospheres. Then, a commercially available guide wire (external diameter: 0.014") was inserted into the tube 3 while keeping the movable part in a bent state.

For the tube 3 of Example 1 and Example 2, the movable part was bent while keeping its external diameter constant. In addition, the guide wire was able to be inserted into the tube 3.

On the other hand, in Comparative Example 1, the external diameter of the movable part increased as compared to those of Example 1 and Example 2. In Comparative Example 2, the movable part was bent, but at a smaller angle than those of Example 1 and Example 2.

The invention is not limited to the description of the embodiments above, but may be altered within the scope of the claims. An embodiment and example based on a proper combination of technical means disclosed in different embodiments and examples are encompassed in the technical scope of the invention.

Industrial Applicability

The present invention makes it possible to provide a catheter (i) having improved kink resistance, (ii) operable even when it is deformed inside a bent blood vessel, and (iii) whose movable part is easily bendable and the movable part thus bent is firmly kept in this shape. More specifically, the present invention is applicable for (a) a microcatheter, (b) a penetration catheter for penetrating a narrowed site, (c) an infusion catheter capable of locally administering a therapeutic agent, (d) a guiding catheter, or (e) the like catheter, which are used in percutaneous transluminal angioplasty or percutaneous transluminal coronary angioplasty which are performed for peripheral blood vessel shaping, coronary artery shaping, valve shaping, and the like.

The invention claimed is:

1. A catheter comprising:
a fluid-driven actuator including:
a balloon;
a restricting member for restricting inflation of the balloon in a short axis direction of the catheter; and
a tube which is less stretchable in a long axis direction of the catheter than the balloon is, through which tube a guide wire or a medical solution passes,
according to a cross-sectional view of the fluid-driven actuator taken along the short axis direction of the catheter, the tube being eccentrically provided with respect to the restricting member,
said catheter further comprising an intermediate member which is less stretchable in the long axis direction of the catheter than the balloon is,
according to the cross-sectional view of the fluid-driven actuator taken along the short axis direction of the catheter, the intermediate member being eccentrically provided in the same direction as the tube is eccentrically provided,
wherein, according to the cross-sectional view of the fluid-driven actuator taken along the short axis direction of the catheter, the intermediate member is in contact with the restricting member, and
wherein the balloon is provided so as to enclose the tube,
wherein the restricting member is a coil,
wherein a wire constituting the coil has a circular cross-sectional surface, and
wherein according to the cross-sectional view of the fluid-driven actuator taken along the short axis direction of the catheter, the catheter has an area where the balloon is not in contact with the restricting member, the area being on a side opposite to one side of the catheter on which one side the intermediate member and the tube are eccentrically provided.

2. The catheter according to claim 1, wherein at least part of the balloon and at least part of the tube are provided inside the coil.

3. The catheter according to claim 1, wherein the tube includes a reinforcing layer.

4. The catheter according to claim 1, wherein the intermediate member is in contact with an entire length of the restricting member.

5. The catheter according to claim 1, wherein the intermediate member is in contact with an inner surface of the restricting member.

6. The catheter according to claim 1, wherein, according to the cross-sectional view of the fluid-driven actuator taken along the short axis direction of the catheter, the intermediate member is inserted into between the restricting member and the balloon.

* * * * *